United States Patent
Kishimoto et al.

(10) Patent No.: US 6,251,613 B1
(45) Date of Patent: Jun. 26, 2001

(54) METHOD FOR DETECTING ANTI-GADII ANTIBODY AND METHOD FOR DIAGNOSING CANCER USING SAID DETECTION METHOD

(75) Inventors: Toshihiko Kishimoto, Yokohama; Taka-aki Tamura; Yasutaka Makino, both of Chiba, all of (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 0 days.

(21) Appl. No.: 09/117,250

(22) PCT Filed: Jan. 27, 1997

(86) PCT No.: PCT/JP97/00174

§ 371 Date: Feb. 16, 1999

§ 102(e) Date: Feb. 16, 1999

(87) PCT Pub. No.: WO97/27485

PCT Pub. Date: Jul. 31, 1997

(30) Foreign Application Priority Data

Jan. 26, 1996 (JP) ........................................ 8-11695

(51) Int. Cl.$^7$ .................................................. G01N 33/53
(52) U.S. Cl. ............................. 435/7.1; 435/4; 435/7.92; 435/7.94; 530/387.1
(58) Field of Search ................................... 435/7.23, 7.1, 435/4, 7.92, 7.94, 183, 188; 514/2; 530/350, 387.1, 387.9, 388.25, 388.85, 391.3

(56) References Cited

U.S. PATENT DOCUMENTS 5,407,802   4/1995   Eisenbarth et al. .

5,691,448 * 11/1997 Baekkeskov et al. .

FOREIGN PATENT DOCUMENTS

| 42 37 244 | 4/1992 | (DE) . |
| WO 92/19972 | 11/1992 | (WO) . |
| WO 94/12529 | 6/1994 | (WO) . |

OTHER PUBLICATIONS

Johnson et al., Cancer Treatment Reviews 2:1–31, 1975.*
Gronowski et al., Clinical Chemistry 41:1532–334, 1995.*
Kishimoto et al., Cancer Research 56:5230–37, Nov. 1996.*
Baekkeskov, et al., "Identificiation of the 64K autoantigen in insulin–dependent diabetes as the GABA–synthesizing enzyme glutamic acid decarboxylase" Nature, vol. 347, Sep. 13, 1990, pp. 151–156.
Michelsen, et al., "Cloning, characterization, and autoimmune recognition of rat islet glutamic acid decarboxylase in insulin–dependent diabetes mellitus" Proc. Natl. Acad. Sci. USA, vol. 88, Oct. 1991, pp 8754–8758.
Kaisakia, et al., "Cloning and characterization of rat cysteine sulfinic acid decarboxylase", Biochimica et Biophysica Acta, Mar. 1, 1995, pp. 79–82, vol. 1262.

* cited by examiner

*Primary Examiner*—Sheela Huff
*Assistant Examiner*—Larry R. Helms
(74) *Attorney, Agent, or Firm*—Pillsbury Winthrop LLP

(57) ABSTRACT

The present invention relates to a method of detecting an anti-GADII antibody, and a method of diagnosing cancer using this detecting method. In particular, it relates to a method of diagnosing cancer by detecting an anti-GADII antibody existing in serum. GADII protein increases upon the occurrence of hepatic cancer, and the antibody against GADII protein also increases upon the occurrence of hepatic cancer. As a result, the occurrence of cancer can be monitored by detecting the anti-GADII antibody.

14 Claims, 6 Drawing Sheets

FIG. IA
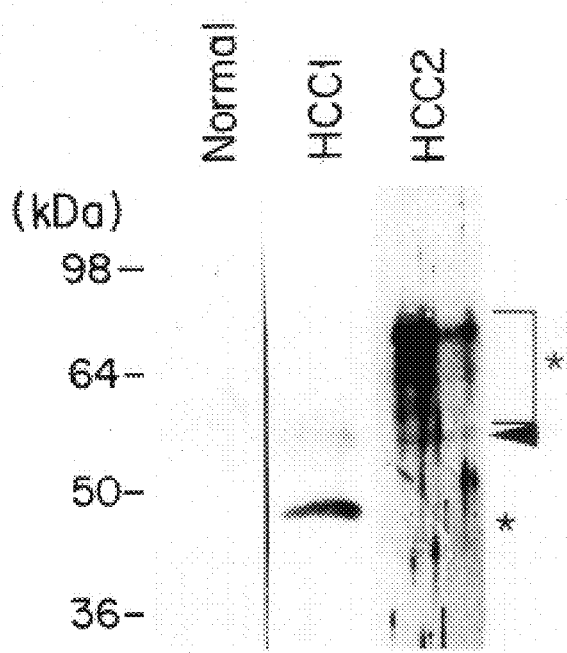
FIG. IB
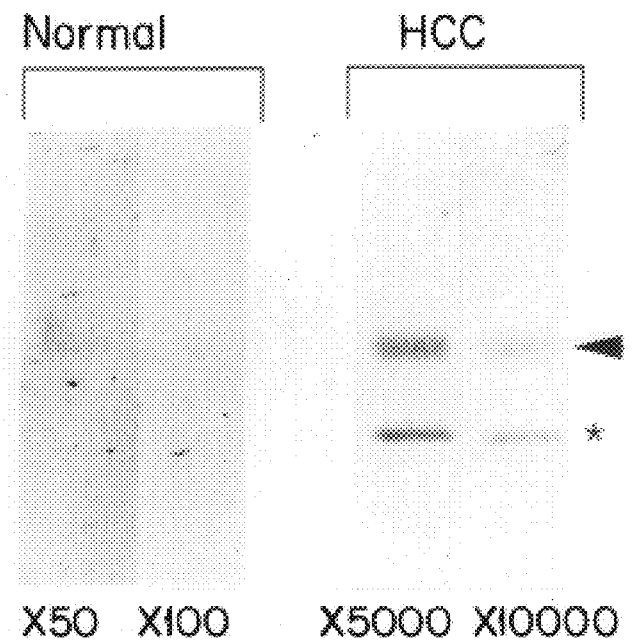

FIG. IC
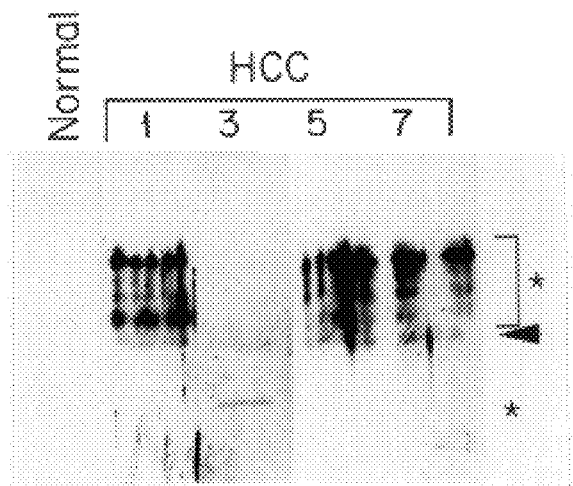
FIG. 2
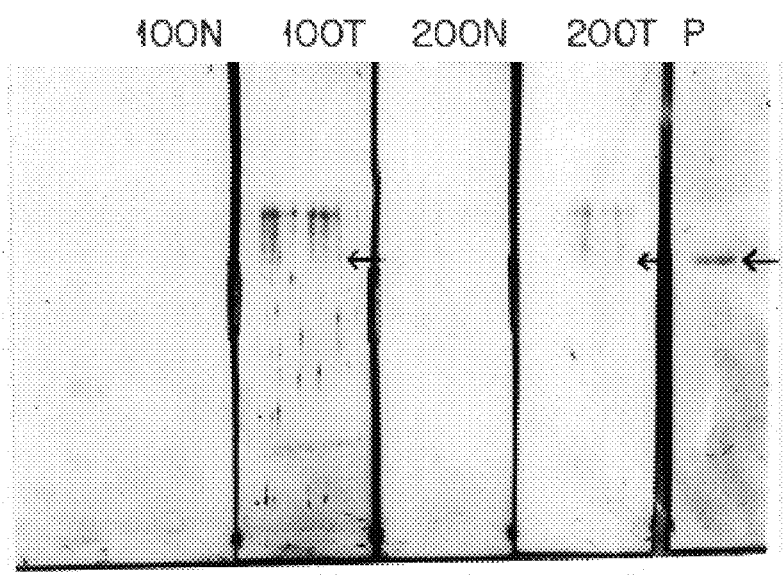

METHOD FOR DETECTING ANTI-GADII ANTIBODY AND METHOD FOR DIAGNOSING CANCER USING SAID DETECTION METHOD

This application is the national phase of international application PCT/JP97/00174 filed Jan. 27, 1997 which designated the U.S.

TECHNICAL FIELD

The present invention relates to a method of detecting an anti-GADII antibody, and a method of diagnosing cancer using this detecting method. In particular, it relates to a method of diagnosing cancer by detecting an anti-GADII antibody existing in serum.

BACKGROUND ART

Cancer is known to occur because of some abnormality in a gene. A change or abnormality in the gene at its transcription level, in particular, is regarded as a major cause of cancer ("Science" Vol. 222, 1983, pp. 765–771). To elucidate the mechanism of onset of cancer, the acquisition of a protein variedly expressed during carcinogenesis and a gene encoding the protein, or a protein different in the state of expression among tissues and a gene encoding the protein has been performed eagerly since about 1980. For example, α-fetoprotein and CEA (carcinoembryonic antigen) are known as cancer-specific proteins which were acquired by biochemically analyzing a carcinomatous tissue, and searching for its difference from a normal tissue.

Nevertheless, only a part of carcinogenesis mechanism has been clarified so far, thus leaving a demand for further elucidation of carcinogenesis-related genes and proteins. Also demanded is a novel method of diagnosing cancer using these carcinogenesis-related genes and proteins.

DISCLOSURE OF THE INVENTION

In order to isolate and elucidate a novel protein whose expression increases during the process of carcinogenesis and a novel gene encoding this protein, the inventors extracted genes specifically expressed in rat hepatic cancer by using subtraction method, and isolated the genes whose expression increased in hepatic cancer according to analysis using dot-screening method. The full length cDNA's of the genes were obtained from a hepatic cancer cDNA library, and the base sequences of the genes were determined. Further, amino acid sequences encoded by the genes were determined.

Moreover, Northern blot hybridization confirmed the cDNA's to be hepatic cancer specific genes. Thus, inventors isolated rat and human GADII genes which were novel genes specific to hepatic cancer. Also, the inventors produced rat GADII protein in *E. coli*, inoculated this protein into a mammal other than a species from which the protein was derived excluding human, to prepare antibodies against the protein and confirm the antigenicity of the protein.

The present invention provides a method of detecting an antibody against the above-mentioned cancer-specific protein, and a method of diagnosing cancer using this detecting method.

The inventors have found that the antibodies against GADII protein which was a cancer-specific protein already invented by the inventors are remarkably detected in a living organism upon carcinogenesis, thereby accomplishing the present invention.

The present invention provides a method of easily screening the onset of cancer by using GADII, which is a protein remarkably expressed in cancer, such as hepatic cancer in particular, so as to detect an antibody against this protein.

BRIEF DESCRIPTION OF THE DRAWINGS

FIG. 1A is a photograph showing the results of Western blotting in which serum of a normal rat and serum of a hepatic cancer rat are each reacted with recombinant GADII protein. The arrow in the drawing indicates the position of GADII protein.

FIG. 1B is a photograph showing the results of Western blotting in which samples of diluted serum from a normal rat and samples of diluted serum from a hepatic cancer rat serum are each reacted with recombinant GADII protein. The values in the drawing indicate dilutions, whereas the arrow indicates the position of GADII protein.

FIG. 1C is a view showing the results of Western blotting in which samples of diluted serum from a normal rat, and samples of diluted serum from a hepatic cancer rat 1, 3, 5, and 7 months after administration of DEN are each reacted with recombinant GADII protein. The arrow in the drawing indicates the position of GADII protein.

FIG. 2 is a view showing the results of Western blotting in which dilutions of serum from a normal rat and from a hepatic cancer rat are each reacted with recombinant GADII protein.

BEST MODE FOR CARRYING OUT THE INVENTION

Figure 3:
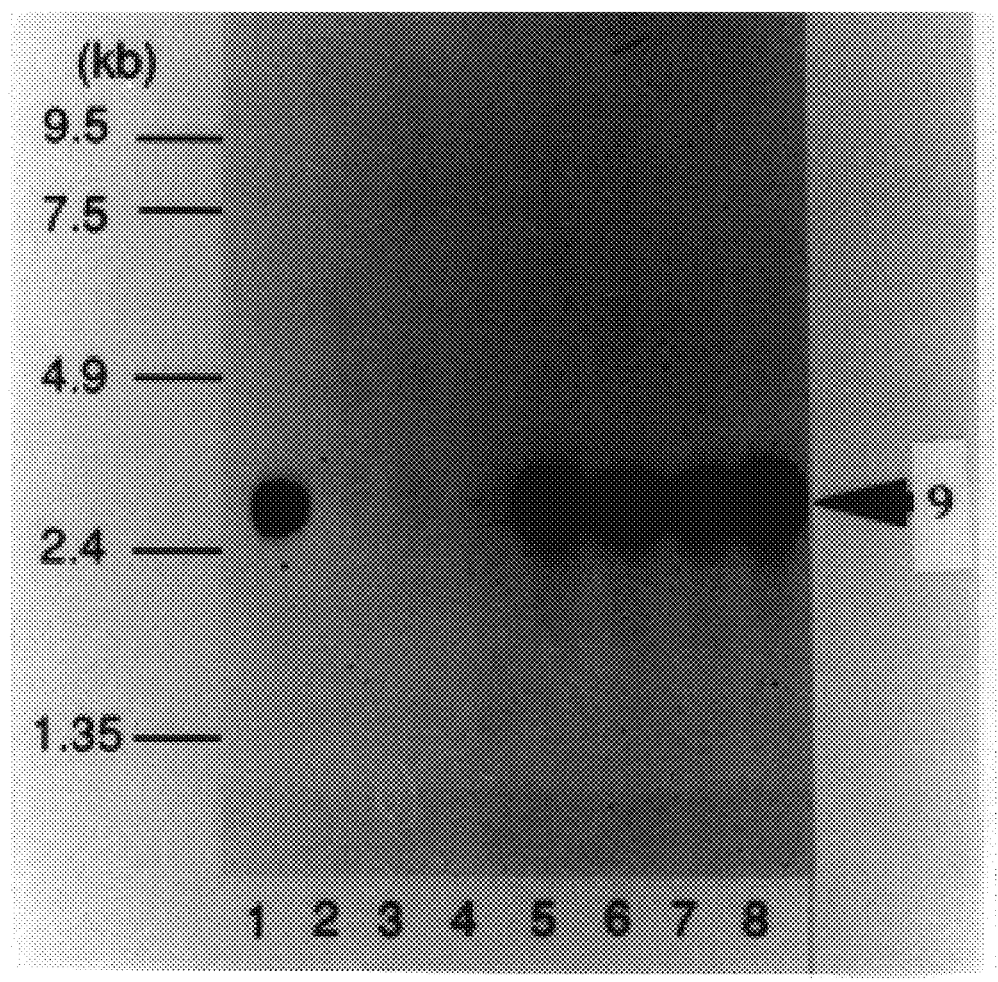
FIG. 3 is a view showing the results of analysis by Northern blot hybridization of mRNA's from normal liver and hepatic cancer with the use of GADII gene as a probe. Lane 1 is a lane for normal liver mRNA, lane 2 is a lane for mRNA of the hepatic cancer 12 hours after administration of DEN, lane 3 is a lane for mRNA of the hepatic cancer 24 hours after DEN administration, lane 4 is a lane for mRNA of the hepatic cancer 48 hours after DEN administration, lane 5 is a lane for mRNA of the hepatic cancer 1 month after DEN administration, lane 6 is a lane for mRNA of the hepatic cancer 3 months after DEN administration, lane 7 is a lane for mRNA of the hepatic cancer 5 months after DEN administration, lane 8 is a lane for mRNA of the hepatic cancer 7 months after DEN administration, and arrow 9 shows the position of the band of GADII mRNA.

As indicated in the prior application, the inventors isolated, from the liver of a rat, a gene remarkably expressed in the liver, determined the base sequence of this gene, and named it GADII gene; and further determined the amino acid sequences of a protein encoded by this gene and named this protein GADII protein. Also, the inventors introduced this GADII gene into E. coli and transformed this gene, thereby expressing recombinant rat GADII protein. Further, by using a probe with respect to GADII gene and an antibody against GADII protein, the inventors confirmed tissue-specific expressions of the gene and protein. Moreover, the inventors isolated human GADII gene by using a human library, determined the base sequence of the gene, and determined the amino acid sequences of the protein encoded by the gene.

The full-length amino acid sequence of GADII protein and full-length gene sequence of GADII gene used in the present invention are respectively described as SEQ ID NO:1 and NO:2 in the Sequence Listing.

As a result of database search, it has been found that, as proteins homologous to a part of amino acid sequence of GADII protein of the present invention, there exist GAD (Proceedings of the National Academy of Science of the United States of America 88, 8754–8758, 1991) and CSAD (Biochemica et Biophysica Acta vol. 1262, pp. 79–82 (1995)).

In the following, the present invention will be explained in detail. Based on the previously obtained finding that expressions of GADII gene and GADII protein are greater in hepatic cancer than in normal liver in a rat as with a human, the inventors studied an easier cancer monitoring method using a rat as a model.

Consequently, it has been found that an anti-GADII antibody (autoantibody) is secreted in the blood of the rat suffering hepatic cancer, and that the anti-GADII antibody in the blood of hepatic cancer rat exists in an amount detectable by ELISA method or Western blot method as shown in Examples, whereby the present invention has been accomplished.

Preferable modes of the present invention are as follows:

1. A method of detecting an anti-GADII antibody in a sample, the method comprising a step of reacting with GADII protein the sample derived from a living organism containing the anti-GADII antibody so as to form a GADII protein/anti-GADII antibody complex, and a step of detecting the GADII protein/anti-GADII antibody complex.

2. Also, the present invention is the detecting method, wherein the sample containing the anti-GADII antibody is serum, lymph, ascitic exudate, or intercellular fluid, preferably serum.

3. Also, the present invention is the method of detecting an anti-GADII antibody recited in 1 or 2, further comprising a step of fixing the GADII protein to a solid support, such as a membrane or microtiter plate, before the sample derived from the living organism containing the anti-GADII antibody is reacted with the GADII protein,.

4. Also, the present invention is the method of detecting an anti-GADII antibody recited in 1 or 2, further comprising a step of isolating the formed GADII protein/anti-GADII antibody complex.

5. Also, the present invention is the detecting method recited in any one of the above, wherein in the step of detecting the GADII protein/anti-GADII antibody complex a labeled anti-Ig antibody is used, for example, an anti-Ig antibody linked with an enzyme such as alkaline phosphatase or radiolabeled anti-Ig antibody.

6. Also, the present invention is the detecting method recited in any one of the above, wherein the GADII protein is recombinant GADII protein.

7. Also, the present invention is a method of diagnosing cancer, hepatic cancer in particular, using any one of the above detecting methods.

8. Also, the present invention is a kit for detecting an anti-GADII antibody, the kit including a reagent containing GADII protein, and preferably further including a reagent containing a labeled anti-Ig antibody, for example, an anti-Ig antibody linked with an enzyme such as alkaline phosphatase or radiolabeled anti-Ig antibody.

9. Also, the present invention is a kit for diagnosing cancer, hepatic cancer in particular, the kit including a reagent containing GADII protein, and preferably further including a reagent containing a labeled anti-Ig antibody, for example, an anti-Ig antibody linked with an enzyme such as alkaline phosphatase or radiolabeled anti-Ig antibody.

10. Also, the present invention is the kit recited in 8 or 9, wherein the GADII protein is recombinant GADII protein.

In the following, the present invention will be explained further in detail.

The GADII protein in the present invention refers to a protein comprising an amino acid sequence described in SEQ ID NO: 1 or 3 in the Sequence Listing or a protein containing this amino acid sequence as part thereof. Further, the GADII protein in the present invention also implies proteins in which the amino acid sequence described in SEQ ID NO: 1 or 3 in the Sequence Listing is partly deleted or replaced or an additional amino acid is inserted therein as long as they generate an antigen-antibody reaction with an anti-GADII antibody in a sample, and polypeptides constituted by a part of the amino acid sequence described in SEQ ID NO: 1 or 3 in the Sequence Listing as long as they are distinguishable from other proteins as an antigen.

In the present invention, in order to detect an anti-GADII antibody, GADII protein is initially prepared. The GADII protein may be either natural GADII protein or that produced by recombination technique. Since there are limitations in terms of quantity and cost on extraction and purification of natural GADII protein from a living organism, however, the GADII protein produced by recombination technique is preferably used. Though the species of origin of GADII protein are not limited in particular as long as the GADII protein reacts with the anti-GADII antibody to be detected, the GADII protein is preferably derived from the species to be inspected. For example, though human GADII protein is more preferably used for detecting a sample derived from a human such as an anti-GADII antibody existing in serum in order to detect human cancer, rat GADII protein can be sufficiently used as long as it reacts with the above-mentioned anti-GADII antibody. In addition, the species of origin of GADII protein are not restricted in particular as long as the GADII protein cross-reacts with the anti-GADII antibody to be inspected; mouse GADII protein and the like can also be used.

In order to prepare recombinant GADII protein, it is necessary to clone GADII gene and cause an appropriate host to transform and express the gene. An example of this method will be explained in detail in Examples described later.

The sample containing an anti-GADII antibody used in the present invention is not restricted in particular as long as it is derived from a living organism and contains an antibody against itself. For example, blood and its preparations such as serum, lymph, ascitic exudate, and intercellular fluid can be listed. Preferable is serum, which is easily available and does not impose an excessive burden on a living organism. The sample derived from a living organism in the present invention includes dilutions of the above-mentioned sample with an appropriate buffer, those processed with addition of a reagent such as heparin, and those roughly or finely purified by use of a separating method such as filtration, centrifuge, or chromatography.

The present invention is characterized in that the GADII protein is subsequently reacted with an anti-GADII antibody to form a GADII protein/anti-GADII antibody complex. The reaction for forming the GADII protein/anti-GADII antibody complex is not restricted in particular as long as it is under a condition where an antigen-antibody reaction occurs, and thus can be appropriately selected according to the conditions to be used, such as the cases where the antigen-antibody reaction is to be generated on a blotting membrane, the reaction is to be generated on a microtiter plate, and the like. For example, in the case where the reaction is to be effected on the blotting membrane, a sample containing an antibody can be dissolved in a buffer such as PBS, so as to be reacted, e.g., at room temperature. In the case where a reaction occurs due to impurities, the sample may be diluted with skim milk or a solution containing a protein such as albumin, so as to ameliorate the background. In the case where it is disadvantageous to effect the reaction at a relatively high temperature due to decomposition of the antigen protein by impurities and the like, the reaction temperature can be set low, e.g., at 4° C. The reaction time, which is not restricted in particular as long as the antigen-antibody reaction sufficiently occurs, may be 30 to 60 minutes, for example. The termination of the reaction is not required in particular, and can be effected by eliminating the sample according to such a method as washing of the membrane with PBS, for example, in the case employing the membrane and washing of wells with PBS after removal of the sample in the case employing the microtiter plate.

In the present invention, before forming the GADII protein/anti-GADII antibody complex, the GADII protein may be fixed to a solid support. As the solid support, membrane, microtiter plate, and the like can be listed, for example. In the case where a membrane is used, a method in which a solution containing GADII protein is directly dropped onto and fixed to the membrane (so-called dot-blot method), Western blot method shown in Examples, and the like can be used. As a method of fixing GADII protein to a microtiter plate, there are a method in which a solution containing GADII protein is introduced into a well and fixated therein; a method in which an anti-GADII antibody prepared beforehand is introduced into and fixed to a well, and then a solution containing GADII protein is added thereto so as to fixate the GADII protein; and the like. The former method employing the microtiter plate is used as so-called ELISA method, whereas the latter is used as sandwich ELISA method. Since the GADII protein used in the present invention can be easily fixed to a plate, using the ELISA method is preferable as there is no need to fixate the anti-GADII antigen. Thus, when GADII protein is fixated before forming the GADII protein/anti-GADII antibody complex, the complex can be isolated easily.

Also, when they are mixed together in a solution or in a gel in the case where GADII protein is not fixated before forming the complex, the antigen-antibody complex is formed by an immunoprecipitation reaction. In this case, before being detected, the GADII protein/anti-GADII antibody complex is preferably separated from other impurities. As its separation method, for example, centrifuge and affinity chromatography with respect to GADII protein can be listed. Specifically, an anti-GADII antibody which has been prepared beforehand is held by a solid support such as gel, and a solution containing the complex is applied thereto, whereby the complex can be collected alone.

Subsequently, in the present invention, the GADII protein/anti-GADII antibody complex is detected. Though the detection method is not restricted in particular, for example, when the above-mentioned dot-blot method, Western blot method, ELISA method, or sandwich ELISA method is employed, a labeled anti-Ig antibody adapted to be bound to Ig of sample-deriving animal species including human may be used for the detection. As the method of labeling the anti-Ig antibody, a method in which an enzyme such as alkaline phosphatase, horseradish peroxidase, or the like is linked to the antibody, a method effecting radiolabeling, and the like can be listed. When an enzyme is used, the detection can be effected according to a coloration reaction. Also, the GADII protein/anti-GADII antibody complex can be detected by use of multistage reactions such as reaction with a biotin-bound anti-Ig antibody and then with an avidin-bound material. These multistage reactions are also included in the concept of the present invention, and the biotin-bound anti-Ig antibody used in the multistage reactions is also included in the labeled anti-Ig antibody in the present invention.

The present invention will now be explained with reference to Examples, which do not limit the present invention.

In order to make the recombinant GADII protein used in the present invention, the isolation, identification, transformation to E. coli, and expression were initially effected. As for enzymes, those manufactured by Takara Shuzo Co., Ltd. were used according to their accompanying manuals, unless otherwise noted.

EXAMPLE 1

Protein Increasing in Expression in Hepatic Cancer and its Gene

I. Isolation of Gene Encoding Protein whose Expression is Increased in Hepatic Cancer 1. Preparation of Hepatic Cancer Rats Hepatic cancer-bearing rats were prepared based on the Salt-Farber method ("Nature", Vol. 263, 1976, pp. 701–703). Actually, 5-week Wistar rats (Funabashi Farm) were intraperitoneally administered diethylnitrosamine (DEN). Two weeks later, oral administration of M Feed (Oriental Yeast) containing 0.02% of 2-aminoacetylfluorene (AAF) was started. One week later, a regenerative hepatic operation was performed. The livers were removed 12, 24, 48 hours and 1, 3, 5 and 7 months after DEN administration, and used for subsequent RNA preparation.

As controls, regenerated livers showing normal growth were acquired by removing the livers 12, 24 and 48 hours after regenerative hepatic operation. These livers were used later for analysis.

2. Preparation of RNA

Total RNA was prepared based on the method described in "Methods in enzymology", Vol. 154 (Academic Press Inc., 1987), pp. 3–28. The actual procedure was as follows:

(1) Three grams of each liver was ground in liquid nitrogen, and added to 100 ml of a 5.5M GTC solution (5.5

M guanidine thiocyanate, 0.5% N-lauronylsarcosine, 25 mM sodium citrate, pH 7.0). The mixture was homogenized with a Potter type homogenizer.

(2) The homogenate was centrifuged for 10 minutes at 3,000 rpm, and then the supernatant was passed 18G needle 10 times and placed on 12 ml of a cesiumtrifluoroacetic acid solution (50% cesiumtrifluoroacetic acid (Pharmacia), 100 mM disodium ethylenediaminetetraacetate (EDTA) (pH 7.0)) with a specific gravity of 1.6 g/ml that had been added in an SW28 swing rotor centrifuge tube (Beckman). The system was separated by the SW28 swing rotor for 24 hours at 25,000 rpm at 15° C.

(3) The precipitate was dissolved in 600 µl of 4M GTC solution (4M GTC, 25 mM sodium citrate pH7.0, 0.5% N-lauroyl sarcosine), and centrifuged at 15,000 rpm, whereafter the solution portion was recovered. Then, 15 µl of 1M acetic acid and 450 µl ethanol were added, and the mixture was centrifuged for 10 minutes at 15,000 rpm, followed by recovering the precipitate.

(4) The precipitate was dissolved in a suitable amount (about 3 ml) of a TE solution (1 mM Tris-Cl (pH 7.5), 1 mM EDTA) (TE solution was added until the precipitate was dissolved). The solution was centrifuged at 15,000 rpm, and the solution portion was recovered.

(5) Phenol/chloroform in the same amount as the amount of the solution was mixed with the solution. The mixture was centrifuged for 10 minutes at 15,000 rpm, and the solution portion was recovered.

(6) To the solution, a 1/10 volume of 3M sodium acetate (pH 5.2) was added, and ethanol in a 2.5-fold amount was added. The mixture was allowed to stand for 20 minutes at −20° C., and then centrifuged at 15,000 rpm. The precipitate was washed with 80% ethanol, and then dried, dissolved in a suitable amount of TE solution, and stored at −80° C. From each liver, 5–7 mg of total RNA was obtained.

(7) PolyA RNA was prepared by use of oligotex dT30 super™ (Nippon Roche) in accordance with an instruction manual attached to it. The amount of the total RNA used was 1 mg per cycle, and polyA RNA was purified with 750 µl of oligotex dT30 super™. In each liver, about 20 µg of polyA RNA was obtained from 1 mg of the total RNA.

3. cDNA Subtraction

This method was performed in accordance with the method of Hara et al. ("Analytical Biochemistry", Vol. 214, 1993, pp. 58–64 (this reference is a part of the instant specification as a result of its citation herein). The actual procedure was as follows:

(1) The polyA RNA used originated from each of the 7-month hepatic cancer and the normal liver, and 15 µg each was used.

(i) The polyA RNA's were each adsorbed by oligotex dT30 super™, and then the synthesis of cDNA was performed in this state. The conditions for the synthetic reaction followed the literature.

(ii) To the cDNA-oligotex dT30 super™ from hepatic cancer, poly dC tail was added using terminal deoxytransferase (TAKARA SHUZO), and cDNA for a sense strand was synthesized by means of EcoRI-(dG)$_{15}$ primer and Taq polymerase (Perkin-Elmer).

Between the sense strand cDNA from the hepatic cancer and the cDNA-oligotex dT30 super™ from the normal liver, the cDNA subtraction reaction was carried out.

(iii) After the reaction, the resulting cDNA solution was amplified by a PCR reaction using both of primers, EcoRI-(dG)$_{15}$ and XhoI-(dT)$_{30}$, in accordance with the method described in "Current Protocols in Molecular Biology" (1987, Greene Publishing Associates and Wiley-Interscience), Chapter 15 unit 15.1. The conditions for the PCR were 25 cycles, each cycle comprising three stages at different temperatures, 94° C. for 90 seconds, then 55° C. for 2 minutes, and then 72° C. for 3 minutes, using the solution of the following composition:

| | |
|---|---|
| cDNA solution | 69 µl |
| 10 × Taq butter (Perkin-Elmer) | 10 µl |
| 1.25 mM dNTP | 16 µl |
| EcoRI-(dG)$_{15}$ primer (2 µg/µl) | 2 µl |
| XhoI-(dT)$_{30}$ primer (2 pg/µl) | 2 µl |
| Taq polymerase (Perkin-Elmer)(5 µ/µl) | 1 µl |
| Total | 100 µl |

(i) After subtraction treatment, the resulting gene library was digested with EcoRI (TAKARA SHUZO). The reaction system employed the following conditions:

| | |
|---|---|
| Gene solution | 10 µl |
| 10 × H buffer (TAKARA SHUZO) | 10 µl |
| EcoRI (TAKARA SHUZO) | 5 µl |
| Sterilized water | 75 µl |
| Total | 100 µl |
| Reaction temperature 37° C. | |
| Reaction time: Overnight | |

(ii) After cleavage with EcoRI, 100 µl phenol/chloroform was mixed with EcoRI digested gene library, and the mixture was centrifuged at 15,000 rpm, followed by recovering the aqueous solution portion. To the solution, 10 µl 3M sodium acetate (pH 5.2) was added, and 250 µl ethanol was further added. Then, the mixture was centrifuged at 15,000 rpm, and the precipitate was recovered.

(iii) The recovered precipitate was washed with 1 ml of 70% ethanol, dried, and then dissolved in 75 µl of sterilized water. The solution was formed into the following composition, which was reacted overnight at 37° C. for cleavage with XhoI:

| | |
|---|---|
| Gene solution | 75 µl |
| 1% BSA (TAKARA SHUZO) | 10 µl |
| 10 × H buffer (TAKARA SHUZO) | 10 µl |
| XhoI (TAKARA SHUZO) | 5 µl |
| Total | 100 µl |
| Reaction temperature 37° C. | |
| Reaction time: Overnight | |

(3) Then, 100 µl phenol/chloroform was mixed with the system, and the mixture was centrifuged at 15,000 rpm, followed by recovering the aqueous solution portion. To the solution, 10 µl 3M sodium acetate (pH 5.2) was added, and 250 µl ethanol was further added. Then, the mixture was centrifuged at 15,000 rpm, and the precipitate was recovered. The precipitate was washed with 1 ml of 70% ethanol, dried, and then dissolved in 100 µl of sterilized water to prepare a gene library solution.

4. Incorporation of Gene after Subtraction into Vector (1) pBluescriptII vector (Stratagene) was digested with EcoRI and XhoI (TAKARA SHUZO). The digesting conditions were the same as in 3.(2).

(2) The digested ends of the digested pBluescriptII vector were dephosphorylated by bacterial alkaline phosphatase for 1 hour at 65° C. and then 100 µl of phenol/chloroform was mixed with the system, and the mixture was centrifuged at 15,000 rpm, followed by recovering the aqueous solution portion. Phenol/chloroform extraction was carried out 3 times.

(3) To the solution, 10 μl 3M sodium acetate (pH 5.2) was added, and 250 μl ethanol was further added. Then, the mixture was centrifuged at 15,000 rpm, and the precipitate was recovered. The precipitate was washed with 1 ml of 70% ethanol, dried, and then dissolved in sterilized water to a concentration of 100 ng/μl.

(4) The gene library solution obtained in 3. and the digested, dephosphorylated pBluescriptII vector were mixed and reacted in accordance with an instruction manual attached to ligation pack™ (Nippon Gene) to insert each gene of the library into the vector.

5. Incorporation of Gene after Subtraction into *E. coli*

In accordance with a customary method, the reaction mixture in 4.(4) was wholly mixed with competent cells of *E. coli*JM109. (TAKARA SHUZO), and reacted for 30 minutes on ice, for 45 seconds at 42° C., and for 3 minutes on ice. Then, 900 μl SOC culture medium was added, and the mixture was allowed to stand for 1 hour at 37° C. to incorporate the vector into the *E. coli*JM109. Then, the *E. coli*JM109 was recovered.

6. Extraction of Gene (1) This *E. coli* was sprinkled over LB agar medium with the following supplements composition, and cultured overnight to form colonies.

Supplements Composition of LB Agar Culture Medium:

| Ampicillin (Wako Pure Chemical) | 100 μg/ml |
| IPTG (TAKARA SHUZO) | 0.1 mM |
| X-gal (TAKARA SHUZO) | 0.004% |

Of the colonies formed, white colonies were selected as inoculum for use in gene screening to be performed later on.

(2) 2,000 kinds of inocula were selected, and were each cultured in a 2 ml LB liquid medium containing 100 μg/ml ampicillin. Then, genes were extracted by the alkali method described in "Molecular Cloning Second Edition" (Cold Spring Harbor Laboratory Press, 1989), pp1.25–1.28.

7. Dot Blot Screening (1) The extracted genes were each blotted to two nylon membranes (Millipore) using Bio Dot (Bio-Rad), and denatured with following condition. hen the denatured gene was immobilized by a UV cross-linker (Stratagene).

(i) The genes were each reacted with a solution of 0.1M sodium hydroxide and 0.15M sodium chloride for 20 seconds.

(ii) Then, the system was reacted with a solution of 0.2M Tris-Cl (pH 7.5) and 0.15M sodium hydroxide for 2 minutes.

(iii) Then, the system was reacted in 2×SSC for 2 minutes.

(2) The hepatic cancer polyA RNA and normal liver polyA RNA prepared in 2. were subjected to a reverse transcription reaction with AMV reverse transcriptase (Seikagaku Kogyo) using radioactive CTP ($\alpha$-$^{32}$P-dCTP) (Amersham) to prepare cDNA probes from the respective polyA RNA's.

(3) The genes fixed to the nylon membranes in (1) were each hybridized with each of the cDNA's prepared in (2) under the following conditions:

(i) Prehybridization Conditions

5×SSC

5×Denhardt's solution 0.1M sodium pyrophosphate (pH 6.8)

50% formamide 0.5% SDS

100 μg/ml yeast tRNA

100 μg/ml denatured salmon sperm DNA

Reaction temperature 42° C.

Reaction time 1 hour (ii) Hybridization Conditions

5×SSC

5×Denhardt's solution 0.1M sodium pyrophosphate (pH 6.8)

50% formamide 0.5% SDS

100 μg/ml yeast tRNA

100 μg/ml denatured salmon sperm DNA cDNA probe prepared in (2) (5×10$^5$ cpm/ml)

Reaction temperature 42° C.

Reaction time 16 hours (4) Then, the nylon membranes were each washed with 500 ml of 2×SSC (containing 0.1% SDS), 0.2×SSC and 0.1×SSC in this order, each for 30 minutes at 60° C., and then subjected to autoradiography. Based on the resulting autoradiograms, selection was made of the genes bound in larger amounts to the hepatic cancer-derived cDNA probe than to the normal liver-derived cDNA probe. At least 31 were confirmed in all. Three out of them were selected, and used for the following experiments:

8. Base Sequencing

Determination of the base sequence was performed in accordance with the method described in "Molecular Cloning Second Edition", Chapter pp.13.42–13.58. Actually, the base sequencing of the genes bound in large amounts to the hepatic cancer cDNA probe was carried out by reading the sequence of the gene portion inserted onto the pBluescriptII by the dideoxyterminator method using T7sequence kit™ (pharmacia).

9. Analysis of Homology

The determined base sequences of the genes were analyzed for homology by referring to the data bank of DDBJ (DNA Data Base of Japan). As a result, these three genes were found to be novel genes without homology. These genes were named CRTI gene, HRPI gene and GADII gene. The respective genes were analyzed in the following manner to know whether their lengths were full lengths:

10. Construction of cDNA Library

From 4 μg of the polyA RNA extracted from the hepatic cancer tissue 7 months after DEN administration, cDNA was synthesized by means of Pharmacia's Time Saver cDNA Synthesis Kit™ in accordance with its instruction manual. The outline of this synthesis is given below.

(1) Reverse transcription reaction was performed using a random primer, and 2nd-strand DNA synthesis reaction was carried out with a DNA polymerase to synthesize double-stranded cDNA. To add NotI/EcoRI adaptors to both ends of the cDNA, the cDNA was treated with T4 DNA ligase. Then ligated cDNA was phosphorelated with polynucleotide kinase. As a result, cDNA having EcoRI restriction enzyme cleavage sites at both ends was obtained.

(2) The cDNA was inserted into λgt11 cloning vector (Pharmacia) by use of T4DNA ligase, and packaged with GIGAPACK Gold™ (Stratagene). Thus, the cDNA was incorporated into the λphage for isolation of the gene.

11. Isolation of Gene

Isolation of the gene was performed in accordance with the method described in "Molecular Cloning Second Edition", pp.2.108–2.120. Its outline is offered below.

(1) The cDNA-containing library constructed in 10. was contacted with Y1090r-*E. coli,* then mixed with NZY medium containing 0.7% agar, and sprinkled on NZY medium plate containing 1.5% agar. Incubation was performed for 6 hours at 42° C. to form plaques containing large amounts of cDNA. Then, a nitrocellulose filter (Immobilon, Millipore's registered trademark, Millipore) was placed on the plate to transfer the plaques onto the filter.

(2) The filter was treated with sodium hydroxide to denature the cDNA in the plaques. The conditions for denaturation were the same as described in 7.(1).

(3) The denatured cDNA was heat-treated for 2 hours at 75° C. to immobilize it, and was used for hybridization. The probe used in the hybridization was a part of the CRTI gene whose base sequence had been determined in 8., that part being randomly labeled with $^{32}$P-dCTP by means of a random labeling kit of Boehringer Mannheim. The conditions for hybridization and the conditions for washing followed the conditions described in the literature(Current Protocols in Molecular Biology (Jhon Wiley & Sons, Inc.), Chapter 6, unit 6.3).

(4) As a result of hybridization, a gene having a longer sequence than the sequence of the probe was obtained from plaques corresponding to positive signals obtained from cDNA fixed to the filter.

According to the procedure described above full-length GADII gene was obtained.

EXAMPLE 2
Determination of Amino Acid Sequences of Hepatic Cancer-specific Protein GADII and Gene Encoding the Proteins I. Rat GADII 1. Large-scale Preparation of Gene The following procedure was performed on GADII gene to prepare the gene obtained in Example 1 on a large scale:

(1) The λ phage recovered from the plaques formed on the NZY agar medium in 11.(4) of Example 1 was suspended in SM solution.

(2) 50 μl of the suspension in (1) and 20 μl of Y1090r-*E. coli* were mixed, and allowed to stand for 15 minutes at 37° C.

(3) Then, the mixed solution in (2) was transferred to 10 ml NZY medium containing 100 μg/ml ampicillin, and cultured for 6 hours at 37° C.

(4) The culture was centrifuged for 5 minutes at 8,000 rpm, and the supernatant was recovered.

(5) To the supernatant, 1 ml of 5M NaCl and 1.1 g of polyethylene glycol 6000 were added and dissolved.

(6) The solution was placed on ice for 1 hour, and then centrifuged for 20 minutes at 4° C. at 10,000 rpm.

(7) The precipitate was recovered and suspended in 700 μl SM solution.

(8) 500 μl chloroform was added to the suspension, and the mixture was stirred to dissolve the remaining *E. coli* cells.

(9) The solution was centrifuged for 10 minutes at 5,000 rpm, and the aqueous phase was recovered.

(10) To the aqueous phase, 1 mg/ml RNaseA and 5 mg/ml DNaseI (both Sigma) were added in an amount of 1 μl each. After the mixture was left to stand at 37° C. for 1 hour, 600 μl of 20% polyethylene glycol 6000 (0.8 M NaCl) was added. The mixture was allowed to stand for 30 minutes on ice.

(11) The system was centrifuged for 20 minutes at 4° C. at 15,000 rpm, and then the precipitate was recovered.

(12) To the precipitate, 500 μl SM solution, 50 μl 5M NaCl and 50 μl 0.5M EDTA were added, and 400 μl phenol was further added. The mixture was stirred to dissolve the phage and liberate cDNA.

(13) The solution was centrifuged for 5 minutes at 15,000 rpm at room temperature, and then the aqueous phase was recovered. To the liquid, 1 ml ethanol was added, and the mixture was centrifuged for 20 minutes at 15,000 rpm. The liquid phase was discarded.

(14) The precipitate was washed with 1 ml of 70% ethanol, and dissolved in 100 μl TE solution (10 mM Tris-Cl pH 8.0, 1 mM EDTA) to obtain DNA solution.

2. Insertion of GADII Gene into Vector

GADII gene was inserted into a vector by the following procedure:

(1) A DNA cleavage system of the following composition was prepared to cut DNA with the restriction enzyme EcoRI (TAKARA SHUZO):

| | |
|---|---|
| DNA solution (prepared in 1.) | 20 μl |
| EcoRI (TAKARA SHUZO) | 2 μl |
| Rnase (Nippon Gene) | 1 μl |
| 10 × H buffer (TAKARA SHUZO) | 10 μl |
| Sterilized water | 67 μl |
| Total | 100 μl |
| Reaction temperature 37° C. | |
| Reaction time 4 hours | |

(2) Then, the system was electrophoresed on 0.7% NuSieve (registered trademark) GTG Agarose (TAKARA SHUZO), and DNA of about 2.1 kbp was cut out. This DNA was recovered by means of GENE CLEAN II (registered trademark, Funakoshi) as in its instruction manual.

(3) pBluescriptII (Stratagene) to hold DNA was cleaved with EcoRI, and then dephosphorylated.

(i) Cleavage with EcoRI was carried out using the following system:

| | |
|---|---|
| pBluescriptII (1 μg/μl) | 2 μl |
| 10 × H buffer | 2 μl |
| EcoRI | 2 μl |
| Sterilized water | 14 μl |
| Total | 20 μl |
| Reaction temperature 37° C. | |
| Reaction time: Overnight | |

(ii) Then, 2 μl of 1M Tris pH 8.0 was added, and 1 μl Bacterial Alkaline Phosphatase (TAKARA SHUZO) was added, followed by leaving the mixture to stand for 1 hour at 65° C.

(iii) Then, phenol/CHCl$_3$ extraction was performed twice in accordance with a customary manner to deactivate the enzymes. After purification by ethanol precipitation, the precipitate was dissolved in TE solution to a concentration of 100 μg/μl.

(4) The DNA obtained in (2) and the pBluescriptII obtained in (3) were reacted using the following system to insert the DNA into the vector:

| | |
|---|---|
| DNA (prepared in (2)) | 5 μl |
| EcoRI-cleaved pBluescriptII(prepared in (3)) | 1 μl |
| 10-fold ligation buffer(Nippon Gene) | 2 μl |
| T4 ligase (Nippon Gene) | 1 μl |
| Sterilized water | 11 μl |
| Total | 20 μl |
| Reaction temperature 16° C. | |
| Reaction time 2 hours | |

3. Incorporation of Gene into *E. coli*

In accordance with a customary method, the reaction mixture containing the vector fitted with GADII gene prepared in 2. was each wholly mixed with competent cells of *E. coli* JM109 (TAKARA SHUZO). The mixture was reacted for 30 minutes on ice, for 45 seconds at 42° C., and for 3 minutes on ice. Then, 900 µl of SOC culture medium was added, and the mixture was allowed to stand for 1 hour at 37° C. to incorporate the vector into the *E. coli* JM109. Then, the *E. coli* JM109 was recovered.

The recombinant *E. coli* having GADII gene introduced therein was deposited at the National Institute of Bioscience and Human-Technology, Agency of Industrial Science and Technology, located at 1-3, Higashi 1 chome, Tsukubashi, Ibaraki-ken 305, Japan, under the accession number FERM P-15165, and was then transferred to international deposition on Sep. 11, 1996 (Accession No. FERM BP-5664).

4. Base Sequencing of Gene (1) The *E. coli* JM109 recovered in 3. was sprinkled on LB agar medium (containing 100 µg/ml ampicillin, 0.1 mM IPTG, 0.004% X-gal), and incubated for 16 hours at 37° C.

(2) Of the colonies formed, white colonies were inoculated into 2 ml LB medium (containing 100 µg/ml ampicillin), and cultured for 16 hours at 37° C.

(3) Then, the culture was centrifuged for 1 minute at 12,000 rpm to harvest the cells, and a plasmid DNA solution was recovered by means of Magic Miniprep (registered trademark, Promega).

(4) A recovered DNA was sequenced using a T7-sequencing kit(Pharmacia) and its handling manual. The obtained base sequence of GADII gene is indicated as SEQ ID NO:2 in the Sequence Listing. Homology search of the resulting GADII gene sequence through a database revealed CSAD gene as a partially homologous sequence. CSAD gene is reported in Biochemica et Biophysica Acta, vol. 1262, pp. 79–82 (1995).

5. Determination of Amino Acid Sequence

The amino acid sequences of GADII was determined by the base sequences determined in 4. The amino acid sequence of GADII as Seq. ID No.1 in the sequence listing.

II. Human GADII

1. Isolation of Full-length Gene

Isolation of the full-length gene was performed in accordance with the method described in "Molecular Cloning Second Edition", pp.2.108–2.120. Its outline is offered below.

(1) cDNA library used was Human Liver 5'-Stretch plus cDNA library (CLONTECH). The cDNA library was contacted with C600-*E. coli*, then mixed with NZY medium containing 0.7% agar, and sprinkled on NZY medium plate containing 1.5% agar. Incubation was performed for 6 hours at 42° C. to form plaques containing large amounts of cDNA. Then, a nitrocellulose filter (Immobilon (registered trademark, Millipore)) was placed on the plate to transfer the plaques onto the filter.

(2) The filter was treated with sodium hydroxide to denature the cDNA in the plaques. The conditions for denaturation were the same as described in 7.(1) of Example 1.

(3) The denatured cDNA was heat-treated for 2 hours at 75° C. to immobilize it, and was used for hybridization. The probe used in the hybridization was the portion from the 65th A to the 611th G of Seq. ID No.2 in the Sequence Listing of the rat GADII gene whose base sequence had been determined in the Example 2.I., that portion being randomly labeled with $^{32}$P-dCTP by means of a random labeling kit of Boehringer Mannheim. The conditions for hybridization and the conditions for washing followed the conditions described in the literature.

(4) As a result of hybridization, full-length human GADII gene was obtained from plaques corresponding to positive signals obtained from cDNA fixed to the filter.

2. Determination of Amino Acid Sequence of Human GADII Gene and Amino Acid Sequence of Human GADII The base sequence of human GADII gene was determined by the same method as in I., i.e., in the following manner:

(1) Large-scale Preparation of Gene

1) λ phage recovered from the plaques formed on the NZY agar medium in 1.(1) was suspended in SM solution.

2) 50 µl of the suspension in 1) and 20 µl of C600-*E. coli* were mixed, and allowed to stand for 15 minutes at 37° C.

3) Then, the mixed solution in 2) was transferred to 10 ml NZY medium, and cultured for 6 hours at 37° C.

4) The culture was centrifuged for 5 minutes at 8,000 rpm, and the supernatant was recovered.

5) To the supernatant, 1 ml of 5M NaCl and 1.1 g of polyethylene glycol 6000 were added and dissolved.

6) The solution was placed on ice for 1 hour, and then centrifuged for 20 minutes at 4° C. at 10,000 rpm.

7) The precipitate was recovered and suspended in 700 µl SM solution.

8) 500 µl chloroform was added to the suspension, and the mixture was stirred to dissolve the remaining *E. coli* cells.

9) The solution was centrifuged for 10 minutes at 5,000 rpm, and the aqueous phase was recovered.

10) To the aqueous phase, 1 mg/ml RNaseA and 5 mg/ml DNaseI (both Sigma) were added in an amount of 1 µl each. After the mixture was left to stand at 37° C. for 1 hour, 600 µl of 20% polyethylene glycol 6000 (0.8 M NaCl) was added. The mixture was allowed to stand for 30 minutes on ice.

11) The system was centrifuged for 20 minutes at 4° C. at 15,000 rpm, and then the precipitate was recovered.

12) To the precipitate, 500 µl SM solution, 50 µl 5M NaCl and 50 µl 0.5M EDTA were added, and 400 µl phenol was further added. The mixture was stirred to dissolve the phage and liberate cDNA.

13) The solution was centrifuged for 5 minutes at 15,000 rpm at room temperature, and then the aqueous phase was recovered. To the liquid, 1 ml ethanol was added, and the mixture was centrifuged for 20 minutes at 15,000 rpm. The liquid phase was discarded.

14) The precipitate was washed with 1 ml of 70% ethanol, and dissolved in 100 µl TE solution (10 mM Tris-Cl pH 8.0, 1 mM EDTA) to obtain DNA solution.

(2) Insertion of human GADII gene into vector

Human GADII gene was inserted into a vector by the following procedure:

1) A DNA cleavage system of the following composition was prepared to cut DNA with the restriction enzyme EcoRI (TAKARA SHUZO):

| | |
|---|---|
| DNA solution (prepared in 1.) | 20 µl |
| EcoRI (TAKARA SHUZO) | 2 µl |
| Rnase (Nippon Gene) | 1 µl |
| 10 × H buffer (TAKARA SHUZO) | 10 µl |
| Sterilized water | 67 µl |
| Total | 100 µl |
| Reaction temperature 37° C. | |
| Reaction time 4 hours | |

2) Then, the system was electrophoresed on 0.7% NuSieve (registered trademark) GTG Agarose (TAKARA SHUZO), and DNA of about 2.1 kbp was cut out. This DNA was recovered by means of GENE CLEAN II (registered trademark, Funakoshi) as in its instruction manual.

3) pBluescriptII (Stratagene) to hold DNA was cleaved with EcoRI, and then dephosphorylated.

(i) Cleavage with EcoRI was carried out using the following system:

| | |
|---|---|
| pBluescriptII (1 μg/μl) | 2 μl |
| 10 × H buffer | 2 μl |
| EcoRI | 2 μl |
| Sterilized water | 14 μl |
| Total | 20 μl |

Reaction temperature 37° C.
Reaction time: Overnight (ii) Then, 2 μl of 1M Tris pH 8.0 was added, and 1 μl Bacterial Alkaline Phosphatase (TAKARA SHUZO) was added, followed by leaving the mixture to stand for 1 hour at 65° C.

(iii) Then, phenol/$CHCl_3$ extraction was performed twice in accordance with a customary manner to deactivate the enzymes. After purification by ethanol precipitation, the precipitate was dissolved in TE solution to a concentration of 100 μg/μl.

4) The DNA obtained in 2) and the pBluescriptII obtained in 3) were reacted using the following system to insert the DNA into the vector:

| | |
|---|---|
| DNA (prepared in 2)) | 5 μl |
| EcoRI-cleaved pBluescriptII(prepared in 3)) | 1 μl |
| 10-fold ligation buffer(Nippon Gene) | 2 μl |
| T4 ligase (Nippon Gene) | 1 μl |
| Sterilized water | 11 μl |
| Total | 20 μl |

Reaction temperature 16° C.
Reaction time 2 hours (3) Incorporation of gene into *E. coli*

In accordance with a customary method, the reaction mixture containing the vector fitted with human GADII gene prepared in (2) was wholly mixed with competent cells of *E. coli* JM109 (TAKARA SHUZO). The mixture was reacted for 30 minutes on ice, for 45 seconds at 42° C., and for 3 minutes on ice. Then, 900 μl of SOC culture medium was added, and the mixture was allowed to stand for 1 hour at 37° C. to incorporate the vector into the *E. coli* JM109. Then, the *E. coli* JM109 was recovered.

The recombinant *E. coli* having human GADII gene introduced therein was named hCSAD2, and deposited at the National Institute of Bioscience and Human Technology (Address: 1-3, Higashi 1-chome, Tsukuba-shi, Ibaraki-ken, Japan), Agency of Industrial Science and Technology, Japan, under the accession number FERM P-15762. Then, the microorganism was transferred to international deposition on Sep. 4, 1996 (Accession No. FERM BP-5653).

(4) Base sequencing of gene

1) The *E. coli* JM109 recovered in (3) was sprinkled on LB agar medium (containing 100 μg/ml ampicillin, 0.1 mM IPTG, 0.004% X-gal), and incubated for 16 hours at 37° C.

2) Of the colonies formed, white colonies were inoculated into 2 ml LB medium (containing 100 μg/ml ampicillin), and cultured for 16 hours at 37° C.

3) Then, the culture was centrifuged for 1 minute at 12,000 rpm to harvest the cells, and a plasmid DNA solution was recovered by means of Magic Miniprep (registered trademark, Promega).

4) The recovered DNA was sequenced with DNA Sequencing Kit (dye terminator method, Perkin-Elmer) to determine the complete base sequence. The base sequence of the DNA is indicated as Seq. ID No. 4 in the Sequence Listing. The homology of the DNA to rat GADII gene (human homology to rat) was 73% for the full length of the gene, and 83% for the protein coding region. The homology was calculated by maximum matching using DINASIS ver 3.0 (Hitachi Software Engineering).

(5) Determination of amino acid sequence

The amino acid sequence of human GADII was determined by the base sequence determined in (4). This amino acid sequence is indicated as Seq. ID No.3 in the Sequence Listing. Its homology to rat GADII (homology of human to rat) is 85%.

EXAMPLE 3

Confirmation of Possibility for Diagnosis of Hepatic Cancer at Gene Expression Level 1. Analysis of Rat GADII Gene by Northern Blot Hybridization The analysis of GADII gene by Northern blot hybridization was made in accordance with the method using formaldehyde denatured gel electrophoresis described in "Current Protocols in Molecular Biology" (1987, Greene Publishing Associates and Wiley-Interscience), Chapter, unit 4.9. PolyA RNA's used in the analysis were (i) polyA RNA derived from a normal liver and that from hepatic cancer 7 months after DEN administration, and (ii) all polyA RNA's of hepatic cancer samples prepared in Example 1.I.2. The amount of the polyA RNA used was 500 ng for each sample.

(1) The GADII gene carried on pBluescriptII in the Example 2.I.2. was cut out of the vector by treatment with a restriction enzyme.

(2) Then, the restriction enzyme-treated solution was subjected to agarose gel electrophoresis to separate the targeted GADII gene.

(3) The GADII gene separated in (2) was purified with GENE CLEAN II (registered trademark, Funakoshi).

(4) The purified GADII gene was labeled by Random Primed DNA Labeling Kit (Boehringer Mannheim) using α-$P^{32}$dCTP (Amersham) in accordance with its instruction manual to make a $^{32}$P-dCTP-labeled HRPI gene probe.

(5) Systems using the normal liver and the 7-month hepatic cancer were each analyzed by Northern blot hybridization using the probe prepared in (4). As a result, GADII gene was detected as a gene significantly increased in hepatic cancer. This finding showed that hepatic cancer and normal liver could be distinguished, namely, the occurrence of hepatic cancer could be monitored, and further hepatic cancer could be diagnosed, by using GADII gene.

(6) Then, systems using all polyA RNA's of the hepatic cancer samples prepared in Example 1.I.2. were each analyzed by Northern blot hybridization using the same probe. The result is shown in FIG. 3. The arrow in FIG. 3 indicates the band position of GADII mRNA. In accordance with induction of cancer, significant increases in GADII gene were noted (FIG. 3). This finding showed that the use of GADII gene would permit the distinction of hepatic cancer at the initial stage, i.e., the monitoring of progress of hepatic cancer, and further the early diagnosis of hepatic cancer. However, the method needs to take a hepatic tissue and to extract the mRNA and amplify the mRNA.

EXAMPLE 4

Expression of GADII

1. Large-scale Preparation of Rat GADII Gene (1) Construction of Recombinant Vector Rat GADII gene was integrated into pET3a vector having a histidine tag incorporated therein as shown in FIG. 3. The details are offered below.

(i) The pBluescriptII vector having GADII gene inserted therein that was constructed in Example 2.1.2. was amplified by the PCR method described in "Current Protocols in Molecular Biology" (Greene Publishing Associates and Wiley-Interscience, 1987), Chapter 15, unit 15.1. For the amplification, primers of the base sequences of the following formulae (1) and (2) were used, and EcoRI site was introduced ahead of the base sequence encoding the first methionine portion of GADII gene.

Formula (1)
5'GAA TTC CCC ATG GCT GAC TCA AAA CCA CTC AGA A 3'

Formula (2)
5'GCA CTG ACC AGA AAT GGC AC 3'

(ii) The amplified gene was cut out by cleavage with EcoRI and SacI.

(iii) Separately, the remaining portion present on the C-terminal side of GADII gene of GADII gene-inserted pBluescriptII was cut with BglII. Then, the residue was smoothed with Klenow fragment, and then cleaved with SacI to cut out the gene.

(iv) The gene cut out in (ii) and the gene cut out in (iii) were ligated together by means of Ligation Pack (Nippon Gene) in accordance with its instruction manual to produce GADII gene.

Figure 4:
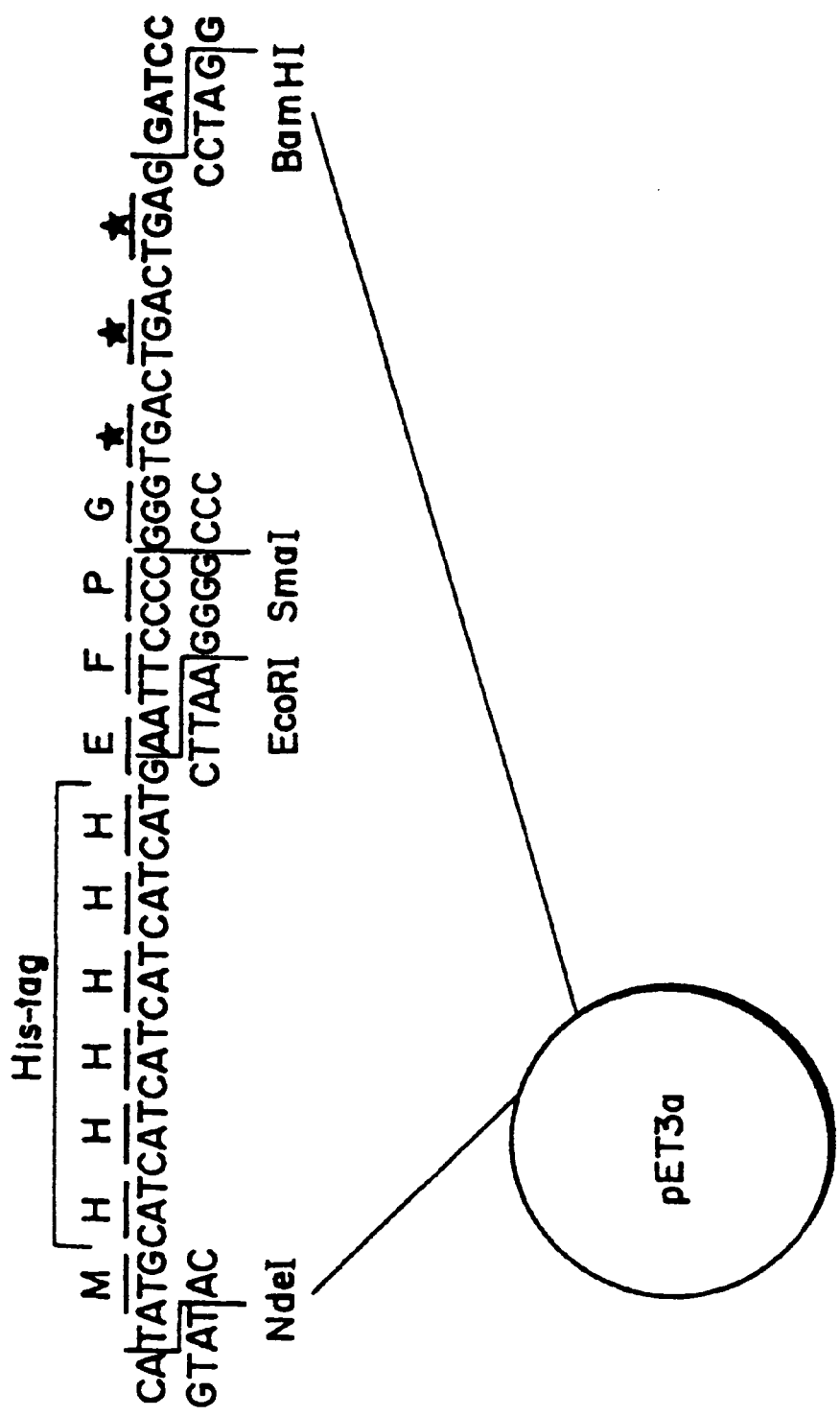
FIG. 4 is a view showing pET3a vector into which a histidine tag has been introduced, which is used for introducing GADII gene and employed in Examples.

(v) pET3a vector having a histidine tag incorporated therein as shown in FIG. 4 was cut with EcoRI and SmaI, and then dephosphorylated.

(iv) The GADII gene prepared in (iv) and the vector constructed in (v) were ligated together by means of Ligation Pack (Nippon Gene) in accordance with its instruction manual.

Confirmation of the gene inserted into the vector during the foregoing process was performed by reading the base sequence of the insert.

(2) Large-scale preparation of GADII gene

The GADII gene-integrated plasmid was prepared on a large scale by the method described in "Molecular Cloning Second Edition" (Cold Spring Harbor Laboratory Press, 1989), pp.1.33–1.52.

2. Expression of GADII (1) The mass-produced plasmid was introduced into *E. coli* BL21 (DE3) pLysS.

(2) The *E. coli* was cultured in LB medium containing 100 μg/ml ampicillin. When turbidity measured with a spectrophotometer (Beckman) reached 0.5 at a wavelength of 600 nm, IPTG was added in a concentration of 0.5 mM to induce the expression of GADII.

3. Purification of GADII (1) Two hours later, *E. coli* cells were recovered, and suspended in Lysis Buffer. The suspension was sonicated at 4° C., and centrifuged for 15 minutes at 18,000 rpm at 4° C. with 50.2 Ti rotor using Beckman Optima XL-80.

(2) Then, the supernatant was taken, and 1M imidazole (pH 7.5) was added to a final concentration of 10 mM. The mixture was purified with Ni-agarose (registered trademark, Qiagen) under non-denaturing conditions in accordance with its instruction manual.

(3) The purified sample was subjected to 10% SDS-PAGE electrophoresis, and stained with Coomassie brilliant blue. A band appeared around 56 kD (FIG. 14), confirming the resulting protein to be GADII protein.

(4) The remaining purified GADII protein was treated with 2×SDS sample buffer and subjected to 5 mm gel thick 10% SDS-PAGE electrophoresis in the same way as in (3). After electrophoresis, the gel was stained with 0.25M KCl for 30 min at 4° C.

(5) The white-stained target band of about 56 kD was cut out with a cutter knife, and the band was further cut to smaller pieces with the cutter knife.

(6) The pieces were subjected to Model 422 electroeluator (Bio-Rad) to elute the protein for 8 hours at 20 mA in accordance with its instruction manual.

(7) The eluted protein was recovered in accordance with the instruction manual of the electroeluator. The protein solution was stored at −80° C.

The recombinant GADII protein obtained by the foregoing operation was used in the method and kit of the present invention. Also, the recombinant GADII protein obtained by the foregoing operation was used for making the following anti-GADII antibody.

EXAMPLE 5

Preparation of Anti-GADII Antibody

1. Preparation of Anti-GADII Antibody

The GADII protein prepared in Example 4 was inoculated into rabbits for immunization in accordance with the method described in "Antibodies, A Laboratory Manual" (Cold Spring Harbor Laboratory Press, 1988), Chapter 5, to produce anti-GADII antibody.

2. Western Blot

The method described in "Current protocols in molecular biology" (Greene Publishing Associates and Wiley-Interscience, 1987), Chapter 10, unit 10.8 was followed.

(1) Western blotting of the GADII protein prepared and purified in Example 4 was performed on a nylon membrane (Immobilon P (Millipore)).

Figure 6:
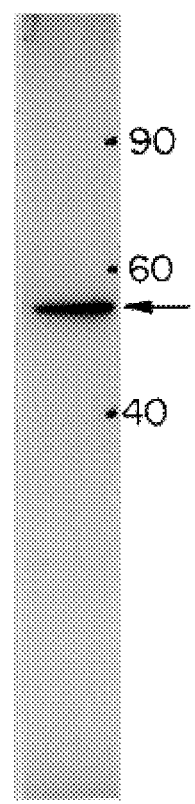
FIG. 6 is a view showing the results of Western blotting in which recombinant GADII protein and an anti-GADII antibody are reacted with each other. The arrow in the drawing represents the position of GADII protein, whereas values indicate molecular weights (kD).

(2) Then, the anti-GADII antibodies were reacted with the GADII protein on the membrane. The complex was reacted with alkaline phosphatase-labeled anti-rabbit IgG antibodies as secondary antibodies. The alkaline phosphatase was further reacted with a substrate (NBT, BCIP (both products of Promega)) for color development. The result was shown in FIG. 6. The numbers in the figure indicate the protein molecular weight in kD unit. The row in the figure indicates the band position of the GADII protein. A band for GADII protein was detected at 56 kD, confirming the anti-GADII antibodies to react with GADII protein.

Similarly, when the antibody of this example was reacted with the recombinant GADII protein obtained from the human GADII gene yielded at II of Example 2, it was found that the antibody of this example also cross-reacted with the human GADII protein.

The anti-GADII antibody obtained here can be used, together with the GADII protein obtained in Example 4, in the sandwich ELISA in the measuring method of the present invention.

EXAMPLE 6

Investigation of Use of GADII Protein in Diagnosing Hepatic Cancer (1) One gram each of the hepatic cancer tissue (7 month after DEN administration) and normal liver tissue prepared in Example 1 was homogenized in 5 ml of 2×SDS sample buffer, and boiled for 3 minutes to obtain the hepatic cancer tissue extract.

(2) The extract and the GADII prepared in Example 4 were subjected to 12.5% SDS-PAGE electrophoresis, and then Western blotted. The amounts of protein were unified by staining the gels, separately electrophoresed similarly, with Coomassie brilliant blue and comparing the colors.

Figure 7:
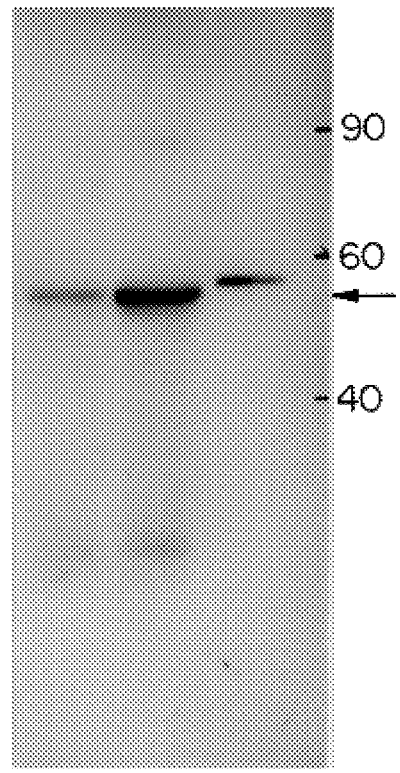
FIG. 7 is a view showing the results of Western blotting in which recombinant GADII protein extracted from a rat liver and the anti-GADII antibody obtained by Example 5 are reacted with each other. The lane at the right end is a lane for recombinant GADII protein, whose molecular weight has increased by the amount corresponding to the histidine tag. The center lane is a lane for the liver tissue extract. The lane at the left end is a lane for the normal rat liver tissue extract.

(3) Then, the extract was reacted with the anti-GADII antibody prepared in Example 5. The complex was reacted with alkaline phosphatase-labeled anti-rabbit IgG antibody as the secondary antibody. The alkaline phosphatase was further reacted with a substrate (NBT, BCID (both products of Promega)) for color development. The results are shown in FIG. 7. In this drawing, numbers indicate molecular weights of the protein in terms of kD. The arrow in the drawing indicates the position of the band of GADII protein. As with the results of Northern blot hybridization, significant increases in GADII protein were confirmed in hepatic cancer and in the process of hepatic cancer occurrence. That is, a correlation was found to exist between the occurrence of hepatic cancer and the increases in GADII protein. In this method, however, it is necessary that a liver tissue be collected from a living organism and that a protein be extracted from the tissue.

EXAMPLE 7
Confirmation of GADII Gene Distribution in Tissues

To confirm the distribution of the genes in various tissues, Rat MTN Blot (registered trademark, CLONTECH) was used. This product is a commercially available membrane blotted with polyA RNA's of rat tissues to be used in the above-mentioned Northern blot hybridization. This membrane was subject to Northern blot hybridization by the method described in "Molecular Cloning Second Edition", (Cold Spring Harbor Laboratory Press, 1989) pp. 7.3–7.84 in accordance with the product's instruction manual with the use of the aforementioned GADII gene probe.

Figure 5:
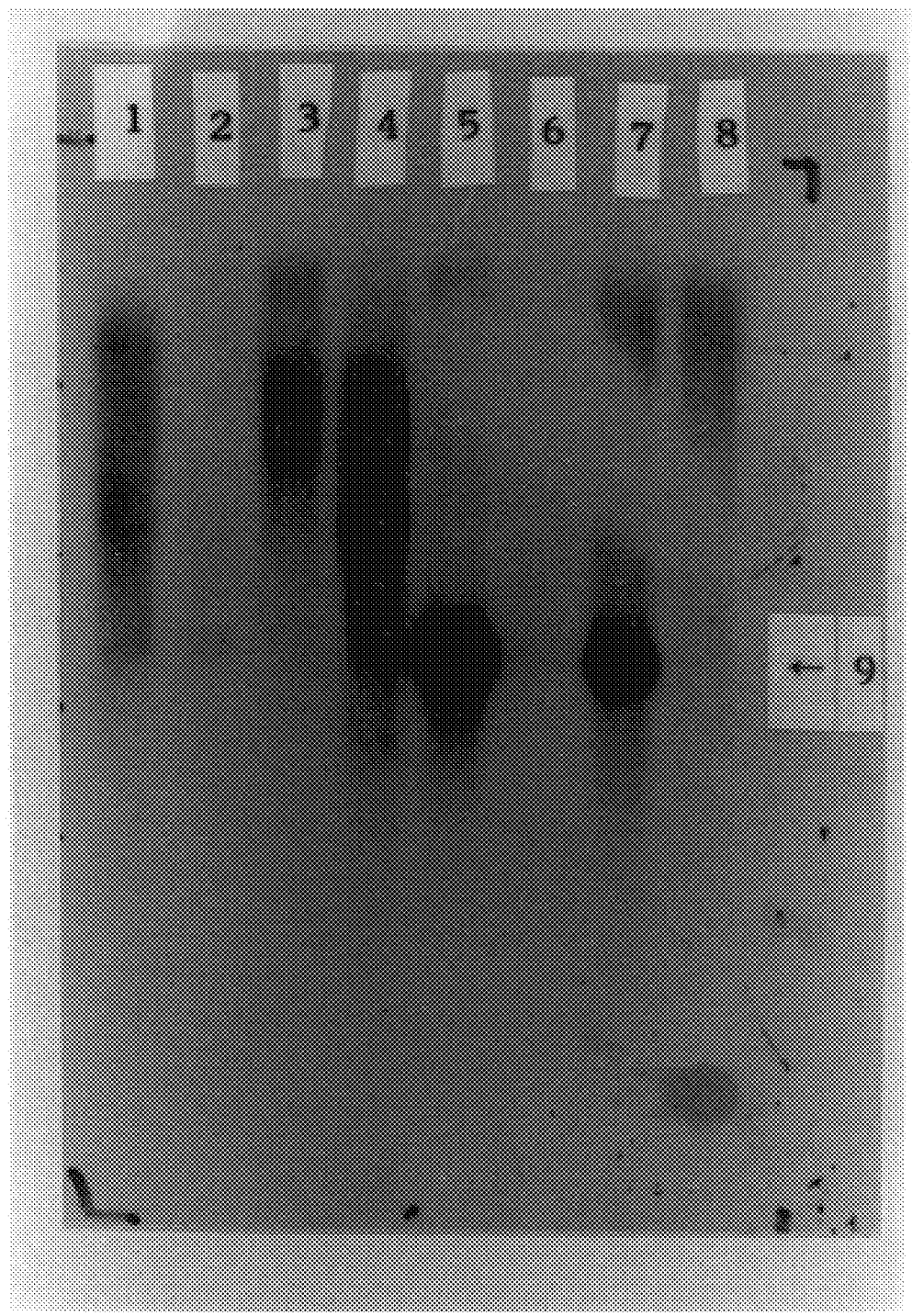
FIG. 5 is a view showing the expression of GADII gene in various organs. Lane 1 is a lane for electrophoresed mRNA, lane 2 is a lane for electrophoresed brain mRNA, lane 3 is a lane for electrophoresed spleen mRNA, lane 4 is a lane for electrophoresed lung mRNA, lane 5 is a lane for electrophoresed liver mRNA, lane 6 is a lane for electrophoresed skeletal muscle mRNA, lane 7 is a lane for electrophoresed kidney mRNA, lane 8 is a lane for electrophoresed testicle mRNA, and arrow 9 indicates the position of the band of GADII mRNA.

The results are shown in FIG. 5. As can be seen from the results, the GADII gene was strongly expressed in liver and kidney, and also was expressed in lungs though with a different length. It indicates that, when expressions of GADII gene and GADII protein increase in renal cancer and stomach cancer, the detection of these expressions allows the occurrences of renal cancer and stomach cancer to be monitored.

EXAMPLE 8
Detection of Anti-GADII Antibody—Western Blot Method

From the foregoing results, it has been found that the expressions of GADII gene and GADII protein increase upon the occurrence of hepatic cancer. Accordingly, by studying a method which can monitor the occurrence of GADII protein more easily, the inventors have found that a rat with the occurrence of hepatic cancer produces an antibody against GADII, and that the occurrence of hepatic cancer can be monitored by measuring this antibody. In the following, this measuring method will be explained.

Western blotting was performed according to the method described in "Current protocol in molecular biology," chapter 10, unit 10.8, so as to detect the GADII antibody. This method will now be described.

(1) After 100 mg of the recombinant GADII protein prepared and purified in Example 4 were subjected to 10% SDS-PAGE electrophoresis, a (pole-type) semidry transfer apparatus manufactured by Nihon Eido Co., Ltd. was used for transferring the protein to an Immobilon P membrane (manufactured by Millipore Corporation). The transfer condition was in conformity to the recommended condition described in the product manual of Nihon Eido Co., Ltd. After the transfer, the membrane was washed with TBS (20 mM Tris-HCl pH 7.5, 150 mM NaCl), and then a 3% skim milk solution (hereinafter simply referred to as skim milk solution) dissolved in TBST (20 mM Tris-HCl pH 7.5, 150 mM NaCl, 0.05% Tween 20) was used for blocking at room temperature for 1 hour.

(2) Then, blood of a normal rat was collected, and serum was prepared according to a conventional method. This serum was diluted with the 3% skim milk solution to various kinds of dilutions which will be mentioned later. Also, the serum of the hepatic cancer rat collected at I.1. in Example 1 was diluted with the 3% skim milk solution to various kinds of dilutions which will be mentioned later. The membrane to which the recombinant GADII protein had been transferred was put into each dilution, and was reacted with the GADII protein at room temperature for 1.0 hour. After the reaction, the membrane was washed with the 3% skim milk solution at room temperature for 5 minutes 3 times, and then was reacted with the alkaline phosphatase-labeled anti-rat IgG antibody (purchased from Promega Corporation) as the secondary antibody. The reaction condition (dilution) was in conformity to its manual. After the reaction, the membrane was washed again 3 times with TBST and 2 times with TBS. Then, the membrane was put into solutions in which NBT and BCID (manufactured by Promega), alkaline phosphatase substrates, had been dissolved respectively by 66 $\mu$l and 33 $\mu$l into 10 ml of an alkaline phosphatase buffer (100 mM Tris-HCl pH 9.5, 100 mM NaCl, 5 mM $MgCl_2$), and coloration reactions were effected. The results are shown in FIGS. 1 and 2.

FIG. 1A is a photograph showing the results of Western blotting where each of solutions in which serum of a normal rat and serums (2 specimens, HCC1 and HCC2) of a hepatic cancer rat 7 months after administration of DEN had been diluted with the 3% skim milk solution to 1/1000 was reacted with GADII protein. "HCC1" and "HCC2" indicate the lanes in which their respective hepatic cancer rat serums were reacted. "Normal" indicates the lane in which the normal rat serum was reacted. The arrow indicates the position of the band of GADII protein, whereas values indicate molecular weights. This photograph confirmed that the anti-GADII antibody was detected from each of the serums of the hepatic rat 7 months after the DEN administration.

FIG. 1B is a photograph showing the results of Western blotting where each of samples in which the serum of a normal rat had been diluted with the 3% skim milk solution to 1/50 and 1/100, respectively, and samples in which the serum of a hepatic cancer rat 7 months after the DEN administration had been diluted with the 3% skim milk solution to 1/5000 and 1/10000, respectively, was reacted with GADII protein. "HCC" indicates the lane in which the serum of the hepatic cancer rat was reacted, whereas "Normal" indicates the lane in which the serum of the normal rat was reacted. The numbers indicate dilutions. The arrow indicates the position of the band of GADII protein. From this photograph, no anti-GADII antibody was detected in the serum from the normal rat even in the sample diluted to 1/50. By contrast, in the serum from the hepatic cancer rat 7 months after the DEN administration, the anti-GADII antibody was detected even in the sample diluted to 1/10000.

FIG. 1C is a photograph showing the results of Western blotting where each of samples in which the serum of a normal rat and serums of a hepatic cancer rat 1, 3, 5, and 7 months after the DEN administration had been diluted with the 3% skim milk solution to 1/1000 was reacted with GADII protein. "HCC" indicates the respective lanes in which the serums of the hepatic cancer rat were reacted, whereas the numbers indicate months elapsed after the DEN administration. "Normal" indicates the lane in which the serum of the normal rat was reacted. The arrow indicates the position of the band of GADII protein. From this photograph, it was confirmed that the GADII antibody was detected from the serum of the hepatic cancer rat 1 month after the DEN administration.

FIG. 2 is a set of photographs showing the results of Western blotting where each of samples in which the serum of a normal rat and the serum of a hepatic cancer rat 7 months after the DEN administration had been diluted with the 3% skim milk solution to 1/1000 and 1/2000 was reacted with GADII protein. "100N" and "200N" indicate reactions with samples in which the serum of a normal rat was diluted to 1/1000 and 1/2000, respectively, whereas "100" and "200T" indicate reactions with samples in which the serum of a hepatic cancer rat was diluted to 1/1000 and 1/2000, respectively. "P" indicates, as a positive control, the reaction with the anti-GADII antibody polyclonal antibody prepared in Example 5. The arrow indicates the position of the band of GADII protein. From these photographs, it was confirmed that the GADII antibody was detected from each of the serums of the hepatic cancer rat 7 months after the DEN administration.

From the foregoing results, it has been found that the anti-GADII antibody reacting with the GADII antibody is remarkably detected from the serum of the rat having hepatic cancer, whereas the anti-GADII antibody in the serum of the normal rat is not greater than its detection limit. Namely, it has been actually demonstrated that the anti-GADII autoantibody exists, and that the anti-GADII autoantibody exists in a free state in the serum of the hepatic cancer rat. Further, it has been demonstrated that the anti-GADII antibody exists in the serum of the hepatic cancer rat in an amount obviously greater than that in the serum of the normal rat. It indicates that, when the anti-GADII antibody expressed in a hepatic cancer rat is detected by utilizing an antigen-antibody reaction by Western blotting employing the recombinant GADII protein, the occurrence of hepatic cancer can be screened. Also, it indicates that hepatic cancer of an animal other than rat may be detected by using the GADII protein of the type of this animal (e.g., human GADII protein). As mentioned above, the inventors have isolated and identified the GADII gene in human as well, whereby there is a high possibility of monitoring the occurrence of human hepatic cancer by detecting the anti-GADII antibody in human.

Western blotting has confirmed that the anti-GADII autoantibody exists in the serum of the hepatic cancer rat. Also, it has been confirmed that GADII is fixed to the membrane film. From these facts, it has been found that the anti-GADII autoantibody can be detected by ELISA method using the antigen-antibody reaction while GADII is fixed to a plate. The operation of ELISA method may be effected, for example, in the following manner.

Detection of Anti-GADII Antibody—ELISA Method (1) A solution in which the recombinant GADII protein prepared and purified in Example 4 had been dissolved into PBS at a concentration of 10 μg/ml was added and fixed to each well of a microtiter plate. Then, the solution was removed.

(2) Samples in which serums of a normal rat and a hepatic cancer rat had been diluted with the 3% skim milk in a doubling fashion were prepared and added to each well so as to effect a reaction.

(5) After being reacted with a peroxidase-labeled anti-rat IgG antibody (purchased from CALTAG Inc.) as the secondary antibody, each well was washed with PBS for 3 times. Subsequently, a peroxidase substrate solution (100 mM citrate buffer pH 4.0, 0.006% $H_2O_2$, 0.3 mg/ml ABTS) was added thereto to effect a coloration reaction, and then a 1.5% oxalic acid solution was added thereto to terminate the reaction. Thereafter, the absorbance at 415 nm was measured.

Also, the method of the present invention can be effected according to sandwich ELISA method using the rabbit's anti-GADII antibody purified from the antiserum prepared in Example 5.

What is claimed is:

1. A method of detecting an anti-GADII antibody in a sample, the method comprising a step of allowing a sample derived from a living organism containing the anti-GADII antibody to bind to GADII protein comprising the amino acid sequence set forth in SEQ ID NO: 1 in the Sequence Listing, so as to form a GADII protein/anti-GADII antibody complex; and a step of detecting said GADII protein/anti-GADII antibody complex.

2. A detecting method according to claim 1, wherein said sample containing the anti-GADII antibody is serum.

3. A method of detecting an anti-GADII antibody according to claim 1, further comprising a step of fixing the GADII protein to a solid support before the sample derived from the living organism containing the anti-GADII antibody is is allowed to bind to the GADII protein.

4. A detecting method according to claim 3, wherein said solid support is a membrane or microtiter plate.

5. A detecting method according to claim 1, further comprising a step of isolating the formed GADII protein/anti-GADII antibody complex.

6. A detecting method according to claim 1, wherein in the step of detecting said GADII protein/anti-GADII antibody complex a labeled anti-Ig antibody is used.

7. A detecting method according to claim 1, wherein said GADII protein is recombinant GADII protein.

8. A method of detecting an anti-GADII antibody in a sample, the method comprising a step of allowing a sample derived from a living organism containing the anti-GADII antibody to bind to GADII protein comprising the amino acid sequence set forth in SEQ ID NO: 3 in the Sequence Listing, so as to form a GADII protein/anti-GADII antibody complex; and a step of detecting said GADII protein/anti-GADII antibody complex.

9. A detecting method according to claim 8, wherein said sample containing the anti-GADII antibody is serum.

10. A method of detecting an anti-GADII antibody according to claim 8, further comprising a step of fixing the GADII protein to a solid support before the sample derived from the living organism containing the anti-GADII antibody is allowed to bind to the to the GADII protein.

11. A detecting method according to claim 10, wherein said solid support is a membrane or microtiter plate.

12. A detecting method according to claim according to claim 8, further comprising a step of isolating the formed GADII protein/anti-GADII antibody complex.

13. A detection method according to claim 8, wherein the step of detecting said GADII protein/anti-GADII antibody complex, a labeled anti-Ig antibody is used.

14. A detecting method according to claim 8, wherein said GADII protein is recombinant GADII protein.

* * * * *

SEQUENCE LISTING

<160> NUMBER OF SEQ ID NOS: 4

<210> SEQ ID NO 1
<211> LENGTH: 506
<212> TYPE: PRT
<213> ORGANISM: Rattus rattus

<400> SEQUENCE: 1

```
Met Ala Asp Ser Lys Pro Leu Arg Thr Leu Asp Gly Asp Pro Val
 1               5                  10                  15

Pro Val Glu Ala Leu Leu Arg Asp Val Phe Gly Ile Val Val Asp
                20                  25                  30

Glu Ala Ile Arg Lys Gly Thr Asn Ala Ser Glu Lys Val Cys Glu
                35                  40                  45

Trp Lys Glu Pro Glu Glu Leu Lys Gln Leu Leu Asp Leu Glu Leu
                50                  55                  60

Gln Ser Gln Gly Glu Ser Arg Glu Arg Ile Leu Glu Arg Cys Arg
                65                  70                  75

Ala Val Ile His Tyr Ser Val Lys Thr Gly His Pro Arg Phe Phe
                80                  85                  90
```

-continued

```
Asn Gln Leu Phe Ser Gly Leu Asp Pro His Ala Leu Ala Gly Arg
             95                 100                 105

Ile Ile Thr Glu Ser Leu Asn Thr Ser Gln Tyr Thr Tyr Glu Ile
            110                 115                 120

Ala Pro Val Phe Val Leu Met Glu Glu Val Leu Lys Lys Leu
            125                 130                 135

Arg Ala Leu Val Gly Trp Asn Thr Gly Asp Gly Val Phe Cys Pro
            140                 145                 150

Gly Gly Ser Ile Ser Asn Met Tyr Ala Ile Asn Leu Ala Arg Phe
            155                 160                 165

Gln Arg Tyr Pro Asp Cys Lys Gln Arg Gly Leu Arg Ala Leu Pro
            170                 175                 180

Pro Leu Ala Leu Phe Thr Ser Lys Glu Cys His Tyr Ser Ile Thr
            185                 190                 195

Lys Gly Ala Ala Phe Leu Gly Leu Gly Thr Asp Ser Val Arg Val
            200                 205                 210

Val Lys Ala Asp Glu Arg Gly Lys Met Ile Pro Glu Asp Leu Glu
            215                 220                 225

Arg Gln Ile Ser Leu Ala Glu Ala Glu Gly Ser Val Pro Phe Leu
            230                 235                 240

Val Ser Ala Thr Ser Gly Thr Thr Val Leu Gly Ala Phe Asp Pro
            245                 250                 255

Leu Asp Ala Ile Ala Asp Val Cys Gln Arg His Gly Leu Trp Leu
            260                 265                 270

His Val Asp Ala Ala Trp Gly Gly Ser Val Leu Leu Ser Arg Thr
            275                 280                 285

His Arg His Leu Leu Asp Gly Ile Gln Arg Ala Asp Ser Val Ala
            290                 295                 300

Trp Asn Pro His Lys Leu Leu Ala Ala Gly Leu Gln Cys Ser Ala
            305                 310                 315

Leu Leu Leu Arg Asp Thr Ser Asn Leu Leu Lys Arg Cys His Gly
            320                 325                 330

Ser Gln Ala Ser Tyr Leu Phe Gln Gln Asp Lys Phe Tyr Asn Val
            335                 340                 345

Ala Leu Asp Thr Gly Asp Lys Val Val Gln Cys Gly Arg Arg Val
            350                 355                 360

Asp Cys Leu Lys Leu Trp Leu Met Trp Lys Ala Gln Gly Gly Gln
            365                 370                 375

Gly Leu Glu Trp Arg Ile Asp Gln Ala Phe Ala Leu Thr Arg Tyr
            380                 385                 390

Leu Val Glu Glu Ile Lys Lys Arg Glu Gly Phe Glu Leu Val Met
            395                 400                 405

Glu Pro Glu Phe Val Asn Val Cys Phe Trp Phe Val Pro Pro Ser
            410                 415                 420

Leu Arg Gly Lys Lys Glu Ser Pro Asp Tyr Ser Gln Arg Leu Ser
            425                 430                 435

Gln Val Ala Pro Val Leu Lys Glu Arg Met Val Lys Lys Gly Thr
            440                 445                 450

Met Met Ile Gly Tyr Gln Pro His Gly Thr Arg Ala Asn Phe Phe
            455                 460                 465

Arg Met Val Val Ala Asn Pro Ile Leu Val Gln Ala Asp Ile Asp
            470                 475                 480

Phe Leu Leu Gly Glu Ala Gly Ala Ser Gly Pro Gly Pro Val Ser
```

```
                485                 490                 595
Cys Phe Leu Ser Leu Pro His Pro Ser Ser Ala
                500                 505

<210> SEQ ID NO 2
<211> LENGTH: 2121
<212> TYPE: DNA
<213> ORGANISM: Rattus rattus
<220> FEATURE:
<221> NAME/KEY: CDS
<222> LOCATION: (65)..(1585)

<400> SEQUENCE: 2
cgcgctctga acccgtcgtc tgaaccctct ctgaaccttc ctgaagctgg aagatttcac    60 cctg atg gct gac tca aaa cca ctc aga acc ctg gat ggg gac cct gtg   109 cct gtg gag gct ttg ctc cgg gac gtg ttt ggg att gtc gta gat gag   157 gcc att cgg aag ggg acc aat gcc tct gag aag gtc tgc gaa tgg aag   205 gag cct gaa gag ctc aag cag ctg ctg gac ttg gag ctg cag agc cag   253 ggc gag tct agg gag cgg atc ctg gag cgc tgc cgg gct gtg att cat   301 tac agt gtc aag act ggt cac ccc cgg ttc ttc aac cag ctc ttc tca   349 gga tta gat ccc cat gct ctg gcc ggg cgc atc att acg gag agc ctc   397 aat acc agc cag tac aca tat gag att gcc ccc gtg ttt gtg ctc atg   445 gaa gag gag gtg ctg aag aaa ctc cgt gcc ctt gtg ggc tgg aac act   493 ggg gat ggg gtc ttc tgt cct ggt ggt tcc atc tct aac atg tac gcc   541 ata aac ctg gcc cgc ttt cag cgc tac cca gac tgc aag cag agg ggc   589 ctc cgg gcc ctg cca ccc ttg gcc ctc ttc act tca aag gag tgc cac   637 tac tcc atc acc aag gga gct gct ttt ctg gga ctt ggc acc gac agt   685 gtc cga gtg gtc aag gct gat gag aga ggg aag atg atc cct gag gat   733 ctg gag agg cag atc agt ctg gca gag gct gag ggc tcg gtg cca ttt   781 ctg gtc agt gcc acc tct ggt acc acc gtg cta ggg gcc ttt gac ccc   829 ctg gat gca att gcc gat gtt tgc cag cgt cac ggg ctg tgg tta cac   877 gtg gat gcc gcc tgg ggt ggg agc gtc ctg ctg tcc cgg aca cac agg   925 cat ctc ctg gat ggg atc cag agg gct gac tcc gtg gcc tgg aac cct   973 cac aag ctt ctc gcc gcg ggg ctg cag tgc tct gct ctt ctc ctc cgg  1021 gac acc tcg aac ctg ctc aag cgc tgc cac ggg tcc cag gcc agc tac  1069 ctc ttc cag caa gac aag ttc tac aac gtg gct ctg gac acc gga gac  1117 aag gtg gtg cag tgt ggc cgc gcc gtg gac tgt ctg aag ctg tgg ctc  1165 atg tgg aag gcg cag ggt ggg caa ggg ctg gag tgg cgc atc gac cag  1213 gcc ttt gct ctc act cgg tac ttg gtg gag gag ata aaa aag cgg gaa  1261 gga ttt gag ttg gtc atg gag ccc gag ttc gtc aac gtg tgc ttc tgg  1309 ttt gtg cct ccc agc ctg cgg ggg aag aag gag agc cca gat tac agc  1357 cag agg ctg tct cag gtg gcc cct gtg ctc aag gag cgc atg gtg aag  1405 aag gga acc atg atg atc ggc tac cag ccc cat ggg acc cgg gcc aac  1453 ttc ttc cga atg gtg gtg gcc aac ccc ata ctg gtc agg gcc gat ata  1501 gac ttc ctt ctg ggc gag gct gga gcg tct ggg cca gga cct gtg agc  1549
```

-continued

```
tgc ttc ctc tct ctg ccc cac cca agc tct gca taa gctcctg ggttcccaaa      1602 agcgaccttt ctaggaaaca gtggccttga ctgtgtgagc ccccacacac taactctcct      1662
agctaagtat tggctgccag acgtgtctaa agcacactac agtctgttct tacgaaatgt      1722
gcttctttta agtcggtcat agtggtacac accgttaata ccagcactgg ggaggcagag      1782
gcagacacaa gcagatctct tgagtttgag gccagcctgg tctacagagc tggcctacac      1842
agaaaaaaaa cctgtctcaa aaaaaaagaa aggaaggaag aaagaaagga aagaaagaa       1902 atatttttca ttaagattat gtctataaaa aattgttatt aatatgagag atatggtacg      1962
atgtattaag aaagctagat atggggttg gggatttagc tcagtggtag agcccttgcc       2022
taggaagcgc aaggccctgg gttcggtccc cagcttcgaa aaaaggaac cacaaaaaaa       2082 acggcccgct ctagaactag tggatccccc ggcctgcag                             2121
```

<210> SEQ ID NO 3
<211> LENGTH: 493
<212> TYPE: PRT
<213> ORGANISM: Homo sapiens

<400> SEQUENCE: 3

```
Met Ala Asp Ser Glu Ala Leu Pro Ser Leu Ala Gly Asp Pro Val
 1               5                  10                  15

Ala Val Glu Ala Leu Leu Arg Ala Val Phe Gly Val Val Asp
                20                  25                  30

Glu Ala Ile Gln Lys Gly Thr Ser Val Ser Gln Lys Val Cys Glu
                35                  40                  45

Trp Lys Glu Pro Glu Glu Leu Lys Gln Leu Leu Asp Leu Glu Leu
                50                  55                  60

Arg Ser Gln Gly Glu Ser Gln Lys Gln Ile Leu Glu Arg Cys Arg
                65                  70                  75

Ala Val Ile Arg Tyr Ser Val Lys Thr Gly His Pro Arg Phe Phe
                80                  85                  90

Asn Gln Leu Phe Ser Gly Leu Asp Pro His Ala Leu Ala Gly Arg
                95                 100                 105

Ile Ile Thr Glu Ser Leu Asn Thr Ser Gln Tyr Thr Tyr Glu Ile
               110                 115                 120

Ala Pro Val Phe Val Leu Met Glu Glu Val Leu Arg Lys Leu
               125                 130                 135

Arg Ala Leu Val Gly Trp Ser Ser Gly Asp Gly Ile Phe Cys Pro
               140                 145                 150

Gly Gly Ser Ile Ser Asn Met Tyr Ala Val Asn Leu Ala Arg Tyr
               155                 160                 165

Gln Arg Tyr Pro Asp Cys Lys Gln Arg Gly Leu Arg Thr Leu Pro
               170                 175                 180

Pro Leu Ala Leu Phe Thr Ser Lys Glu Cys His Tyr Ser Ile Gln
               185                 190                 195

Lys Gly Ala Ala Phe Leu Gly Leu Gly Thr Asp Ser Val Arg Val
               200                 205                 210

Val Lys Ala Asp Glu Arg Gly Lys Met Val Pro Glu Asp Leu Glu
               215                 220                 225

Arg Gln Ile Gly Met Ala Glu Ala Glu Gly Ala Val Pro Phe Leu
               230                 235                 240

Val Ser Ala Thr Ser Gly Thr Thr Val Leu Gly Ala Phe Asp Pro
               245                 250                 255
```

```
Leu Glu Ala Ile Ala Asp Val Cys Gln Arg His Gly Leu Trp Leu
            260                 265                 270

His Val Asp Ala Ala Trp Gly Gly Ser Val Leu Leu Ser Gln Thr
            275                 280                 285

His Arg His Leu Leu Asp Gly Ile Gln Arg Ala Asp Ser Val Ala
            290                 295                 300

Trp Asn Pro His Lys Leu Leu Ala Ala Gly Leu Gln Cys Ser Ala
            305                 310                 315

Leu Leu Leu Gln Asp Thr Ser Asn Leu Leu Lys Arg Cys His Gly
            320                 325                 330

Ser Gln Ala Ser Tyr Leu Phe Gln Gln Asp Lys Phe Tyr Asp Val
            335                 340                 345

Ala Leu Asp Thr Gly Asp Lys Val Val Gln Cys Gly Arg Arg Val
            350                 355                 360

Asp Cys Leu Lys Leu Trp Leu Met Trp Lys Ala Gln Gly Asp Gln
            365                 370                 375

Gly Leu Glu Arg Arg Ile Asp Gln Ala Phe Val Leu Ala Arg Tyr
            380                 385                 390

Leu Val Glu Glu Met Lys Lys Arg Glu Gly Phe Glu Leu Val Met
            495                 400                 405

Glu Pro Glu Phe Val Asn Val Cys Phe Trp Phe Val Pro Pro Ser
            410                 415                 420

Leu Arg Gly Lys Gln Glu Ser Pro Asp Tyr His Glu Arg Leu Ser
            425                 430                 435

Lys Val Ala Pro Val Leu Lys Glu Arg Met Val Lys Glu Gly Ser
            440                 445                 450

Met Met Ile Gly Tyr Gln Pro His Gly Thr Arg Gly Asn Phe Phe
            455                 460                 465

Arg Val Val Val Ala Asn Ser Ala Leu Thr Cys Ala Asp Met Asp
            470                 475                 480

Phe Leu Leu Asn Glu Leu Glu Arg Leu Gly Gln Asp Leu
            485                 490
```

<210> SEQ ID NO 4
<211> LENGTH: 1926
<212> TYPE: DNA
<213> ORGANISM: Homo sapiens
<220> FEATURE:
<221> NAME/KEY: CDS
<222> LOCATION: (72)..(1553)

<400> SEQUENCE: 4

```
cggcgcgcct gtaatcccag cactctggga gaccgagatt cttggttgat gcaaatcaaa      60
tagagatcct g atg gct gac tca gaa gca ctc ccc tcc ctt gct ggg gac      110 cca gtg gct gtg gaa gcc ttg ctc cgg gcc gtg ttt ggg gtt gtt gtg      158 gat gag gcc att cag aaa gga acc agt gtc tcc cag aag gtc tgt gag      206 tgg aag gag cct gag gag ctg aag cag ctg ctg gat ttg gag ctg cgg      254 agc cag ggc gag tca cag aag cag atc ctg gag cgg tgt cgg gct gtg      302 att cgc tac agt gtc aag act ggt cac cct cgg ttc ttc aac cag ctc      350 ttc tct ggg ttg gat ccc cat gct ctg gcc ggg gcg att atc act gag      398 agc ctc aac acc agc cag tac aca tat gaa atc gcc ccc gtg ttt gtg      446 ctc atg gaa gag gag gtg ctg agg aaa ctg cgg gcc ctg gtg ggc tgg      494
```

-continued

```
agc tct ggg gac gga atc ttc tgc cct ggt ggc tcc atc tcc aac atg       542
tat gct gta aat ctg gcc cgc tat cag cgc tac ccg gat tgc aag cag       590
agg ggc ctc cgc aca ctg ccg ccc ctg gcc cta ttc aca tcg aag gag       638
tgt cac tac tcc atc cag aag gga gct gcg ttt ctg gga ctt ggc acc       686
gac agt gtc cga gtg gtc aag gct gat gag aga ggg aaa atg gtc ccc       734
gag gat ctg gag agg cag att ggt atg gcc gag gct gag ggt gct gtg       782
ccg ttc ctg gtc agt gcc acc tct ggc acc act gtg cta ggg gcc ttt       830
gac ccc ctg gag gca att gct gat gtg tgc cag cgt cat ggg cta tgg       878
ctg cat gtg gat gct gcc tgg ggt ggg agc gtc ctg ctg tca cag aca       926
cac agg cat ctc ctg gat ggg atc cag agg gct gac tct gtg gcc tgg       974
aat ccc cac aag ctc ctc gca gca ggc ctg caa tgc tct gca ctt ctt      1022
ctc cag gat acc tcg aac ctc aag cgc tgc cat ggg tcc cag gcc          1070
agc tac ctt ttc cag cag gac aag ttc tac gat gtg gct ctg gac acg      1118
gga gac aag gtg gtg cag tgt ggc cgc cgt gtg gac tgt ctg aag ctg      1166
tgg ctc atg tgg aag gca cag ggc gat caa ggg ctg gag cgg cgc atc      1214
gac cag gcc ttt gtc ctt gcc cgg tac ctg gtg gag gaa atg aag aag      1262
cgg gaa ggg ttt gag cta gtc atg gag cct gag ttt gtc aat gtg tgt      1310
ttc tgg ttc gta ccc ccc agc ctg cga ggg aag cag gag agt cca gat      1358
tac cac gaa agg ctg tca aag gtg gcc ccc gtg ctc aag gag cgc atg      1406
gtg aag gag ggc tcc atg atg att ggc tac cag ccc cac ggg acc cgg      1454
ggc aac ttc ttc cgt gtg gtt gtg gcc aac tct gca ctg acc tgt gct      1502
gat atg gac ttc ctc ctc aac gag ctg gag cgg cta ggc cag gac ctg      1550
tga gccttctctg tcttgctgcc ggccttgata ccacccctca cccgcagagt           1603
cactgcattc cctcccagcc tttgaggccg ggtgcagtgg ctcacgcctg taatcccagc    1663
actttgggag gccgaggcgg gtggatcact tgaggtcagg agttcgagac cagcctggcc    1723
aataaggtga aaccctgtct ctactaaaaa tacaaaaatt agccgagcat ggtggcctgt    1783
gcctgtaaac ccagctactc aggaggttgg ggcagaattg cttgaaccca gggggcagag    1843
gttgcagtga gccgagattg cacccctgca ctccaggctg ggcaacagta cgagactctg    1903
ttccaaaaaa aataaaaaag ccg                                            1926
```